United States Patent [19]

Takahashi et al.

[11] Patent Number: 5,385,829
[45] Date of Patent: * Jan. 31, 1995

[54] METHOD OF ASSAYING FOR ACYL-L-CARNITINES AND SHORT-CHAIN ACYL-CARNITINES

[75] Inventors: Mamoru Takahashi; Shigeru Ueda, both of Shizuoka, Japan

[73] Assignee: Asahi Kasei Kogyo Kabushiki Kaisha, Tokyo, Japan

[*] Notice: The portion of the term of this patent subsequent to Nov. 30, 2010, has been disclaimed.

[21] Appl. No.: 774,221

[22] Filed: Oct. 9, 1991

[30] Foreign Application Priority Data

Oct. 9, 1990 [JP] Japan .................. 2-270784

[51] Int. Cl.$^6$ .................. A61K 37/00; C12Q 1/44; C12N 9/16; C12N 1/20
[52] U.S. Cl. .................. 435/19; 424/93.4; 435/196; 435/252.1; 435/829; 436/815
[58] Field of Search .................. 435/196, 829, 19, 196, 435/252.01, 829; 424/93; 436/815

[56] References Cited

U.S. PATENT DOCUMENTS

| | | | |
|---|---|---|---|
| 4,221,869 | 9/1980 | Vandecasteele et al. | 435/117 |
| 4,542,098 | 9/1985 | Vandecasteele et al. | 435/190 |
| 4,751,182 | 6/1988 | Sih | 435/128 |
| 4,906,568 | 3/1990 | Jung et al. | 435/128 |
| 4,918,012 | 4/1990 | Nakayama et al. | 435/128 |
| 5,041,375 | 8/1991 | Nakayama et al. | 435/128 |
| 5,156,966 | 10/1992 | Takahashi et al. | 435/190 |
| 5,173,416 | 12/1992 | Takahashi et al. | 435/188 |
| 5,266,463 | 11/1993 | Takahasi et al. | 435/26 |

OTHER PUBLICATIONS

R. Golan et al, *Quantitative Enz. Assay of Short-Chain Acylcarnitines, ect.*, Aug. 16, 1979, pp. 264–267.

"D. The Assay of Long–Chain Acyl–(–)–carnitine ($C_{12}$ and Upward)$^{27}$", *Methods in Enzymology*, vol. 14, pp. 621–622.

"Measurement of Carnitine and O–Acylcarnitines", *Methods in Enzymology*, vol. 72, By L. Bieber et al., pp. 276–287.

"Improved Radiochemical Assay for Carnitine and Its Derivatives in Plasma and Tissue Extracts", *Clinical Chemistry*, vol. 24, No. 1, 1978, By J. Pace et al., pp. 32–35.

"Carnintine Ester Hydrolase of Rat Liver", *The Journal of Biological Chemistry*, vol. 244, No. 16, 1969, By S. Mahadevan et al., pp. 4448–4453.

"Reinigung und Eigenschaften der Carnitindehdrogenase aus Pseudomonas aeruginosa", *European Journal of Biochemistry*, vol. 6, By H. Aurich et al., pp. 196–201.

Primary Examiner—Douglas W. Robinson
Assistant Examiner—Deborah K. Ware
Attorney, Agent, or Firm—Young & Thompson

[57] ABSTRACT

A method of assaying for acyl-L-carnitines including short chain acyl-carnitines including acetyl-L-carnitine and propionyl-L-carnitine in a substance, comprises subjecting a sample of the substance to be analyzed to an enzymatic hydrolysis using an acyl-carnitine esterase. The esterase is produced by *Alcaligenes sp.* FERM BP-2570 and it has substrate specificity for acyl-L-carnitines including short-chain acyl-carnitines. In addition the esterase demonstrates substrate specificity for acetyl-L-carnitine and propionyl-L-carnitine. The enzyme facilitates the hydrolysis reaction of one mole each of the acyl-L-carnitines with one mole of water in which to form one mole each of the corresponding fatty acid and L-carnitine. The amount of the fatty acid and L-carnitine formed is determined by this method.

13 Claims, 8 Drawing Sheets

METHOD OF ASSAYING FOR ACYL-L-CARNITINES AND SHORT-CHAIN ACYL-CARNITINES

FIELD OF THE INVENTION

The invention relates to a novel acyl-carnitine esterase which is useful for analyzing acyl-L-carnitines in, for example, biochemical clinical inspections, screening inspections in food products and so on; a process for the production thereof; and a process comprising the use thereof for analyzing acyl-L-carnitines.

BACKGROUND OF THE INVENTION

L-carnitine, called also vitamin Bγ, is a substance necessary for the transportation of fatty acids through mitochondrial membranes in animals. In the cells of animals, there are also acylated derivatives of L-carnitine, namely, acyl-L-carnitines. Acyl-L-carnitines are excreted from the animal and are found in urine. Therefore, quantitative determination of the content of acyl-L-carnitines in blood etc. is very important in, for example, monitoring the existence of functional disorders of mitochondria in order to detect any defect in the intramuscular energy transference in animals.

THE PRIOR ART

Heretofore, the analysis of acyl-L-carnitines in substances to be examined has been effected by hydrolyzing the acyl-L-carnitines with alkali and determining the amount of liberated free L-carnitine quantitatively. Several reports have proposed the conditions of such hydrolysis of acyl-L-carnitines, for example, Pearson et al. in "Methods in Enzymology", Vol. 14, 621 (1969), Bieber et al. in "Methods in Enzymology", Vol. 72, 276 (1981) and Pace et al. in "Clin. Chem.", 24, 32 (1978).

These prior techniques suffer from significant shortcomings in that the analysis procedures require considerable time and in that the use of a highly concentrated alkali solution for the hydrolysis is dangerous in operation and causes dilution of the sample solution.

In order to overcome such shortcomings, the use of an appropriate enzyme, i.e. an acyl-carnitine esterase, may be considered. There is known an acyl-carnitine esterase originating from liver of rat (S. Mahadevan and F. Sauer, "J. Biol. Chem.", 244, 4448–4453 (1969). This acyl-carnitine esterase has, however, no activity for short-chain acyl-L-carnitines such as acetyl-L-carnitine and propionyl-L-carnitine existing in human blood and, in addition, it has higher Km values for long chain acyl-L-carnitines, such as $3.2 \times 10^{-3}$M for decanoyl-L-carnitine and $5 \times 10^{-3}$M for palmitoyl-L-carnitine, so that a large amount of the esterase is required for achieving complete hydrolysis of these long-chain acyl-L-carnitines. Moreover, in spite of the high demand for the esterase, only 3.7 units of the esterase can be collected from 50 g of rat liver, i.e. from one whole liver of a rat.

Therefore, it has long been desired to find an acyl-carnitine esterase, which exhibits enough enzymatic activity for short-chain acyl-L-carnitines, has lower Km values for substrates and is sufficiently stable, and to develop a reliable and highly sensitive method for the quantitative analysis of acyl-L-carnitines including the short-chain acyl-L-carnitines mentioned above that exist in animals.

SUMMARY OF THE INVENTION

The present inventors have conducted an exhaustive search for acyl-carnitine esterases which meet the above requirements, among a vast number of culture products of bacteria, and have found that a bacterium of the genus Alcaligenes produces an acyl-L-carnitine esterase exhibiting a high activity for short-chain acyl-L-carnitines and that accordingly makes it possible to provide a method for the highly sensitive quantitative determination of acyl-L-carnitines contained in substances to be examined by using it as the hydrolyzing enzyme.

Thus, the present invention provides an acyl-carnitine esterase which has substrate-specificity for acyl-L-carnitine, comprising short-chain acyl-carnitines including acetyl-L-carnitine and propionyl-L-carnitine, and catalyzes the hydrolysis reaction of one mole of each of the acyl-L-carnitines with one mole of water to form one mole of the corresponding fatty acid and one mole of L-carnitine.

The present invention also provides a process for the production of said acyl-carnitine esterase, which comprises cultivating an acyl-carnitine-esterase-producing bacterium that belongs to the genus Alcaligenes in a suitable culture medium and collecting the thus-produced acyl-carnitine esterase from the cultured mixture.

The present invention further provides a process for quantitatively analyzing acyl-L-carnitines comprising short-chain acyl-carnitines including acetyl-L-carnitine and propionyl-L-carnitine, in specimens to be examined, which comprises subjecting a sample of such specimens to be examined to an enzymatic hydrolysis using said acyl-carnitine esterase and then determining the amount of the liberated fatty acids or L-carnitine thus formed, by an analytical technique known per se.

DETAILED DESCRIPTION OF THE INVENTION

Figure 1:
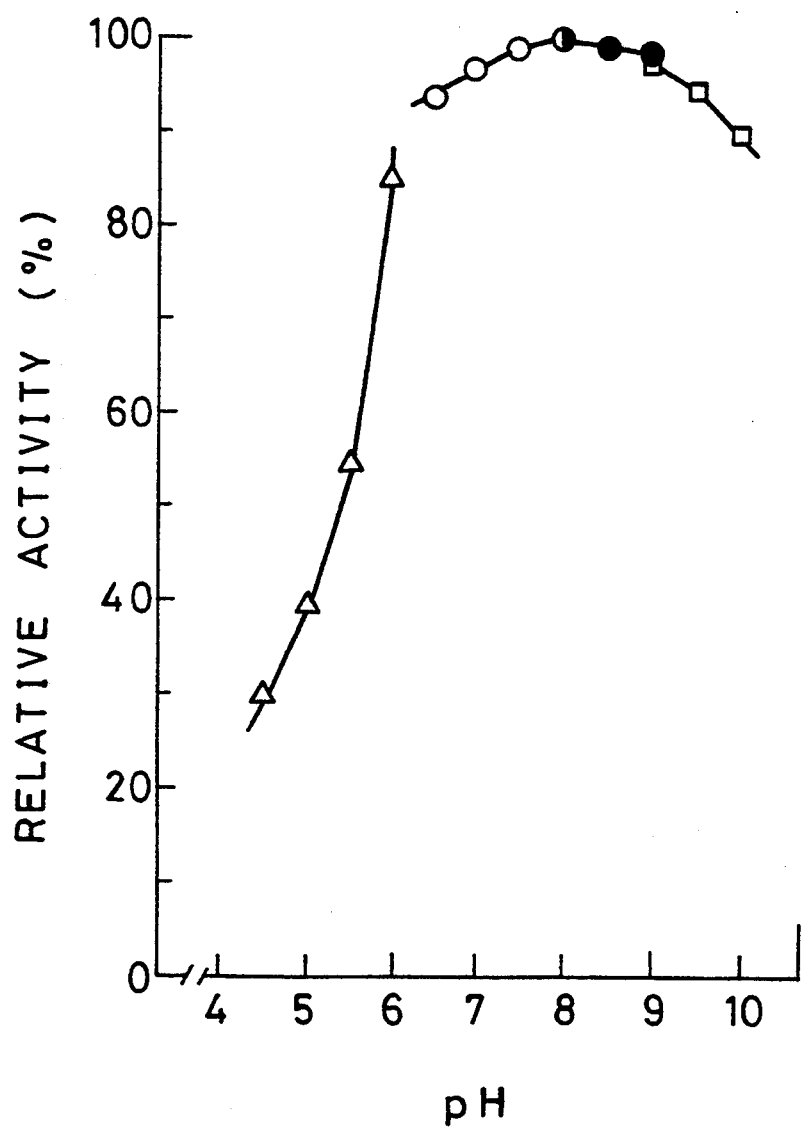
FIG. 1 is a graph showing the optimum pH of the acyl-carnitine esterase according to the present invention.

It is believed that there are a plurality of acyl-carnitine-esterase-producing bacteria that belong to the genus Alcaligenes. One example thereof is the bacterium of bacterial strain No. 981 which has been isolated by the inventors and has shown activity according to the present invention (hereinafter, this bacterial strain is sometimes referred to as the present bacterial strain). The bacteriological properties of this bacterium are as follows:

A. Morphological Properties

By observing the isolated bacterium after cultivation at 28°–30° C. for 18–24 hours, the following was noted:

It is a straight or somewhat curved rod-like bacterium having round ends existing individually or double linked or occasionally in short chains. No spore formation, moving with peripheral flagella, no polymorphism, size 0.4–0.6 × 1.2–2.5 μm.

B. Growth on Various Media

Observation upon cultivating at 28°–30° C. for 18–24 hours in various culture media gave the following results:

1. Nutrient agar slant medium:
The growth is better, growing filiform. Wet and lustrous in appearance and ocher colored with no production of soluble pigment.

2. Nutrient agar plate medium:
A circular, convex and fully rimmed colony with smooth wet surface; ocher to light ocher colored. No production of soluble pigment.

3. Liquid medium (aqueous peptone):
Growth is better, uniformly turbid. In a long term culture (over 40 hours), formation of pellicle is observed.

4. BCP milk medium:
Becomes alkaline after 4–5 days.

C. Physiological Properties

In the following, the marks denote: $+$ = positive, $(+)$ = weakly positive, $-$ = negative:

| | |
|---|---|
| Grain strain | − |
| KOH reaction | + |
| Capsule formation | − |
| Acid fast staining | − |
| OF-test (Hugh Leifson) | No change |
| OF-test ($NH_4H_2PO_4$ as N-source) | O (oxidation) |
| Growth in aerobic condition | + |
| Growth in anaerobic condition | − |
| Growth at | |
| 41° C. | − |
| 37° C. | + |
| 15° C. | + |
| Halotolerance at | |
| 0% | + |
| 5% | + |
| 7% | − |
| Growth at pH | |
| 4.6 | − |
| 5.4 | + |
| 8.9 | + |
| 9.8 | − |
| Gelatin hydrolysis | − |
| Starch hydrolysis | − |
| Casein hydrolysis | − |
| Esculin hydrolysis | − |
| Cellulose hydrolysis | − |
| Tyrosine hydrolysis | − |
| Production of catalase | + |
| Production of oxidase | + |
| LV reaction | |
| Production of urease (SSR) | − |
| Production of urease (Chris) | − |
| Production of indol | − |
| Production of $H_2S$ (detected by acetate paper) | − |
| Production of acetoin ($K_2HPO_4$) | − |
| Production of acetoin (NaCl) | − |
| MR test | − |
| Nitrate reduction tests | |
| Detection of gas | + |
| Detection of $NO_2^-$ | − |
| Detection of $NO_3^-$ | − |
| Utilization of Simmons medium for | |
| citrate | + |
| malate | + |
| maleate | − |
| malonate | (+) |
| propionate | − |
| gluconate | − |
| succinate | + |
| Utilization of Christenssen medium for | |
| citrate | + |
| malate | + |
| maleate | + |
| malonate | + |
| propionate | − |
| gluconate | + |
| succinate | + |
| Production of gas from glucose | − |
| Acid-production from | |
| adonitol | − |
| L(+)-arabinose | (+) |
| cellobiose | − |
| dulcitol | − |
| meso-erythritol | − |
| fructose | − |
| galactose | + |
| glucose | + |
| glycerin | (+) |
| inositol | − |
| inulin | − |
| lactose | − |
| maltose | − |
| mannitol | − |
| mannose | + |
| melezitose | − |
| melibiose | − |
| raffinose | − |
| L(+)-rhamnose | − |
| D-ribose | − |
| salicin | − |
| L-sorbose | − |
| starch | − |
| saccharose | − |
| trehalose | + |
| xylose | − |
| Accumulation of poly-β-hydroxybutyrate | − |

D. Utilization of Carbon Sources

Experiments for examining the utilization of various carbon sources by cultivating in a liquid culture medium (pH 7.0) containing 5 g of a carbon source, 5 g of NaCl, 0.2 g of $MgSO_4 \cdot 7H_2O$, 1.0 g of $NH_4H_2PO_4$ and 1 liter of distilled water gave the following results:

| | |
|---|---|
| Glucose | + |
| L(+)-arabinose | − |
| Fructose | + |
| Mannitol | − |
| Mannose | + |

-continued

| | |
|---|---|
| Gluconate | + |
| Acetate | + |
| Adipate | − |
| Pimelate | + |
| Suberate | + |
| Tartrate | + |

For the identification of the bacterium described above, the procedures according to "Guide for the Identification of Bacteria in Medicine: Microbiological Method", Vol 3, 2nd Ed. were employed and the identification was made by comparison of the experimental results with the data given in "Bergey's Manual of Determinative Bacteriology", 8th Ed "Bergey's Manual of Systemic Bacteriology", Vol. 1 (1984) and ibid., Vol 2 (1986).

As given above, the present bacterial strain may be described as a Gram negative rod-shaped bacterium moving with its peripheral flagella, producing catalase and oxidase and not producing acid from glucose in a medium containing peptone (Hugh-Leifson) but causing oxidative decomposition of glucose with the production of acid, showing no formation of spores and no polymorphism and growing under aerobic conditions.

Gram negative bacteria which are characterized by rod-shaped bacterial cells and which grow under aerobic conditions and move with peripheral flagella are those of the genera Alcaligenes, Chromobacterium and Flavobacterium. Bacteria of the genus Chromobacterium produce purple pigment and those of the genus Flavobacterium produce yellow pigment. Since the bacterial strain according to the present invention does not produce any pigment, it is evident that it belongs to the genus Alcaligenes.

In order to determine the species of Alcaligenes to which the present bacterial strain belongs, the characteristic properties of the present bacterial strain were compared with those of three bacterial species given in "Bergey's Manual of Systematic Bacteriology", Vol. 1 (1984), namely *Alcaligenes faecalis* (in the following, this is represented sometimes by "F"), *Alcaligenes denitrificans subsp. denitrificans* (in the following, this is represented sometimes by "D") and *Alcaligenes denitrificans subsp. xylosoxidans* (in the following, this is represented sometimes by "X"). The results are given below.

In the following comparison, the mark "+" means a positive probability of over 90%, the mark "−" means a negative probability of over 90% and the mark "d" means that the property is judged to be neither positive nor negative.

| Properties | F | D | X | This Strain |
|---|---|---|---|---|
| Production of oxidase | + | + | + | + |
| Reduction of nitrate | − | + | + | + |
| Reduction of nitrate | + | + | + | + |
| Gelatin hydrolysis | − | − | − | − |
| Production of acid in OF-medium for | | | | |
| Xylose | − | − | + | − |
| Glucose | − | − | + | − |
| Utilization of carbon source for | | | | |
| Glucose | − | − | + | + |
| L(+)-arabinose | − | − | − | − |
| Fructose | − | − | d | + |
| Mannitol | − | − | − | − |
| Mannose | − | − | d | + |
| Gluconate | − | + | + | + |
| Acetate | + | + | + | + |

From the results of the above comparison, it was observed that the present bacterial strain has properties which are in accordance with those of *Alcaligenes subsp. xylosoxidans* as to many categories but are different therefrom as to acid productivity in OF culture media and as to production of acid from xylose.

Accordingly, the present bacterial strain was judged to be distinct from these known bacterial species and therefore was deposited in Institute of Microbiological Engineering of the Agency of Industrial Science and Technology, Japan, under the designation *Alcaligenes sp.* No. 981 with the Deposit No. Bikoken Jo-ki 2570 (FERM BP-2570).

For obtaining the acyl-carnitine esterase according to the present invention, an acyl-carnitine-esterase-producing bacterium belonging to the genus Alcaligenes is first cultivated in a suitable culture medium.

As the acyl-carnitine-esterase-producing bacterium mentioned above, the bacterial strain of the above-mentioned *Alcaligenes sp.* No. 981 is the first to be enumerated. But as the bacteriological properties of a bacterium can in general vary, every bacterial strain belonging to the genus Alcaligenes and capable of producing an acyl-carnitine esterase may be employed in accordance with the present invention. Such bacterial strains may be those derived from artificial mutation induced by UV irradiation, radiation, by the use of a mutagen agent such as N-methyl-N-nitro-N-nitrosoguanidine, ethyl methanesulfonate and so on, or may be those derived from natural mutation.

The culture of the bacterium can be conducted under the conditions employed generally for bacterial culture. It is preferred, however, to carry out the culture in a culture medium containing an acyl-L-carnitine. As the acyl-L-carnitine, for example, octanoyl-L-carnitine which is inexpensive may preferably be used (0.1-1%, based on the weight of the culture medium).

As the culture medium, nutrient culture media containing a carbon source capable of being anabolized by the bacteria, a nitrogen source capable of being digested by the bacteria and, as required, inorganic salts and so on may be employed.

For the carbon source capable of being anabolized by the bacteria, there may be employed, for example, glucose, fructose, saccharose, sucrose, molasses, olive oil and so on, either alone or in combination.

For the nitrogen source capable of being digested by the bacteria, there may be employed, for example, peptone, meat extract, yeast extract, corn steep liquor, choline hydrochloride and so on, either alone or in combination.

In addition, inorganic salts such as phosphates and salts of magnesium, calcium, potassium, sodium and heavy metals such as iron, manganese and so on, may be employed as required.

It is of course possible to employ other carbon sources and nitrogen sources capable of being anabolized or digested by the bacteria.

The culture is effected under aerobic conditions, preferably with shaking or aeration agitation; and it is preferred for industrial production to employ submerged aeration culture with agitation.

While the temperature for the culture may be varied within the range in which the acyl-carnitine-esterase-producing bacterium can grow with production of this esterase, it is preferred usually to employ a temperature in the range from 18° to 37° C., especially about 28° C. Although the duration of culture may be different for each specific culture condition, the culture may be terminated at an adequate stage at which the maximum production of the esterase is reached, e.g. usually after 1–3 days or so.

Needless to say, the culture conditions, such as composition and liquid nature of the culture medium, temperature, agitation rate, aeration rate and so on, may be appropriately adjusted and selected so as to achieve desirable results in accordance with each specific bacterial strain employed and the external conditions prevailing. If foaming occurs during liquid culture, an antifoaming agent such as silicone oil, vegetable oil or so on may be employed.

The acyl-carnitine esterase produced is retained mainly within the bacterial cells. Therefore, the bacteria cells are collected from the culture product mixture by any suitable technique such as filtration, centrifugation or so on, and the collected bacterial cells are subjected then a cell-breaking treatment such as mechanical breaking by ultrasonication, treatment with French press, glass beads treatment or freezing-thawing or the like or enzymatic digestion using lysozyme or so on, or a suitable combination of these mechanical and enzymatic means, to obtain a crude liquor containing the acyl-carnitine esterase.

From the crude extract, purified acyl-carnitine esterase can be obtained by known processes for isolating and purifying proteins, enzymes and so on. Thus, the recovery of the esterase can be achieved by, for example, the so-called salting-out method by adding ammonium sulfate, sodium sulfate, potassium sulfate, potassium phosphate, aluminum chloride and so on to the crude extract containing the acyl-carnitine esterase. The precipitate thus obtained may further be purified, as required, using any of various molecular sieves or by means of chromatography, electrophoresis, ultracentrifugation or a combination of these. In practice, the purification can be achieved by making use of the properties of the acyl-carnitine esterase to be isolated. For example, the precipitate obtained as above is first dissolved in water or in a buffer solution and then, after dialyzing it if required, the solution is subjected to molecular sieve chromatography using an ion-exchange resin such as DEAE-cellulose, DEAE-Sephacel, DEAE-Sepharose or DEAE-Sephadex A-50 (products of the Pharmacia Corp.) or DEAE-Toyopearl (Toso Corp.), or using a gel filtration medium such as Sephadex G-100 and G-75 or Sephacryl S-200 or so on. Combinations of these purification means may also be employed. The purified solution thus obtained can be stabilized by adding a stabilizing agent, for example a sugar such as mannitol, saccharose or sorbitol; an amino acid, such as glutamic acid, glycine or so on; or bovine serum albumin etc. as peptide or protein, whereupon the solution is subjected to, for example, lyophilization etc., to obtain a purified product comprising acyl-carnitine esterase.

The characteristic properties of the isolated acyl-carnitine esterase according to the present invention are as given below:

1. Enzymatic activity:

It catalyzes the hydrolysis reaction of an acyl-L-carnitine with water to form L-carnitine and the corresponding liberated free fatty acid:

acyl-L-carnitine + $H_2O$ → fatty acid + L-carnitine

2. Molecular weight: 63,000 ± 7,000

The molecular weight was determined by chromatography using TSK Gel G3000 SW (a product of Toso Corp.) on a column of 0.75 × 60 cm using an eluent consisting of an 0.1M phosphate buffer solution (pH 7.0) containing 0.2M NaCl with the use of the following standard molecular weight markers supplied by Oriental Yeast Co. Ltd.:

| Molecular Weight | Marker Compound |
|---|---|
| 12,400 | Cytochrome C |
| 32,000 | Adenylate kinase |
| 67,000 | Enolase |
| 142,000 | Lactate dehydrogenase |
| 290,000 | Glutamate dehydrogenase |

3. Isoelectric point: pH 5.1 ± 0.5

The isoelectric point was determined by so-called isoelectric focussing using a carrier ampholyte under the condition of a constant voltage of 700 V for 40 hours, whereupon the solution was subjected to fractionation and each fraction was examined for the enzymatic activity.

4. Km value:

Solutions of acyl-carnitines in 100 mM tris-HCl buffer solution (pH 8.0) were prepared in such a manner that concentrations of each acyl-carnitine of $1 \times 10^{-5}$M, $2 \times 10^{-5}$M, $3 \times 10^{-5}$M, $5 \times 10^{-5}$M, $10 \times 10^{-5}$M, $20 \times 10^{-5}$M and $40 \times 10^{-5}$M were achieved, for each of which the Km value for each specific acyl-carnitine was determined. As acyl-carnitines, either those available on the market or those prepared from L-carnitine (a product of Sigma) according to the procedures of Bohemer & Bremer described in "Biochim. Biophys. Acta", 152, 559–567 (1968) were employed.

| Acyl-carnitine | Km Value |
|---|---|
| Acetyl-carnitine | ca. $4 \times 10^{-5}$ M |
| Propionyl-carnitine | ca. $3 \times 10^{-5}$ M |
| Hexanoyl-carnitine | ca. $2 \times 10^{-5}$ M |
| Octanoyl-carnitine | ca. $2 \times 10^{-5}$ M |
| Decanoyl-carnitine | ca. $2 \times 10^{-5}$ M |
| Lauroyl-carnitine | ca. $2 \times 10^{-5}$ M |
| Myristoyl-carnitine | ca. $2 \times 10^{-5}$ M |
| Palmitoyl-carnitine | ca. $3 \times 10^{-5}$ M |
| Stearoyl-carnitine | ca. $5 \times 10^{-5}$ M |

5. Substrate specificity:

Acyl-carnitine solutions in 100 mM tris-HCl buffer solution (pH 8.0) were prepared so that the concentration of each acyl-carnitine was 0.5 mM. Each of the acyl-carnitine solutions was subjected to an enzymatic hydrolysis reaction at 37° C. for 10 mins., whereupon the amount of L-carnitine formed was determined by the L-carnitine analysis method described hereinafter, in order to compare the enzymatic activity of the carnitines. It was found that the highest activity was that of octanoyl-L-carnitine. Moreover, it was also found that the acyl-carnitine esterase originating from liver of rat did not exhibit enzymatic activity for acetyl-L-carnitine and for propionyl-L-carnitine, whereas the esterase according to the present invention had a substantial activity for these short-chain acyl-carnitines.

| Acyl-carnitine | Enzymatic Activity in Relative % |
| --- | --- |
| Acetyl-carnitine | 17 |
| Propionyl-carnitine | 46 |
| Hexanoyl-carnitine | 85 |
| octanoyl-carnitine | 100 |
| Decanoyl-carnitine | 72 |
| Lauroyl-carnitine | 60 |
| Myristoyl-carnitine | 61 |
| Palmitoyl-carnitine | 41 |
| Stearoyl-carnitine | 11 |

6. Optimum pH:

Octanoyl-L-carnitine solutions, in 100 mM acetate buffer solution (pH 4.5–6.0), in 100 mM phosphate buffer solution (pH 6.5–8.0), in 100 mM tris-HCl buffer solution (pH 8.0–9.0) and in 100 mM glycine/NaOH buffer solution (pH 9.0–10.0) were prepared with a concentration of octanoyl-carnitine of 0.5 mM for each of the solutions. Each of these solutions was subjected to an enzymatic hydrolysis reaction at 37° C. for 10 hours and the amount of L-carnitine formed thereby was determined. The results of the analysis of L-carnitine are shown on the graph of FIG. 1, which shows the optimum pH at about 8.0, wherein high enzymatic activities above 90% were reached within a wide pH range from 6.5 to 9.5.

In the graph of FIG. 1, the marks $\triangle$, $\bigcirc$, $\bullet$ and $\square$ correspond to acetate buffer solution, phosphate buffer solution, tris-HCl buffer solution and glycine/NaOH buffer solution, respectively.

7. pH Stability:

Solutions of the esterase according to the present invention in 100 mM acetate buffer solution (pH 4.5–6.0), in 100 mM phosphate buffer solution (pH 6.5–8.0), in 100 mM tris-HCl buffer solution (pH 8.0–9.0) and in 100 mM glycine/NaOH buffer solution (pH 9.0–10.0) were prepared with the concentration of the esterase 0.1 Unit/ml for each of the solutions. Each solution was heat treated at 60° C. for 30 mins., whereupon the residual activity was determined. The results are shown in FIG. 2, which shows that the esterase was stable in the phosphate buffer solution of pH 7.5 and in the tris-HCl buffer solutio of pH 8.5, wherein high enzymatic activities above 90% were reached within a wide pH range from 5.5 of acetate buffer solution to 10.5 of glycine/NaOH buffer solution.

Figure 2:
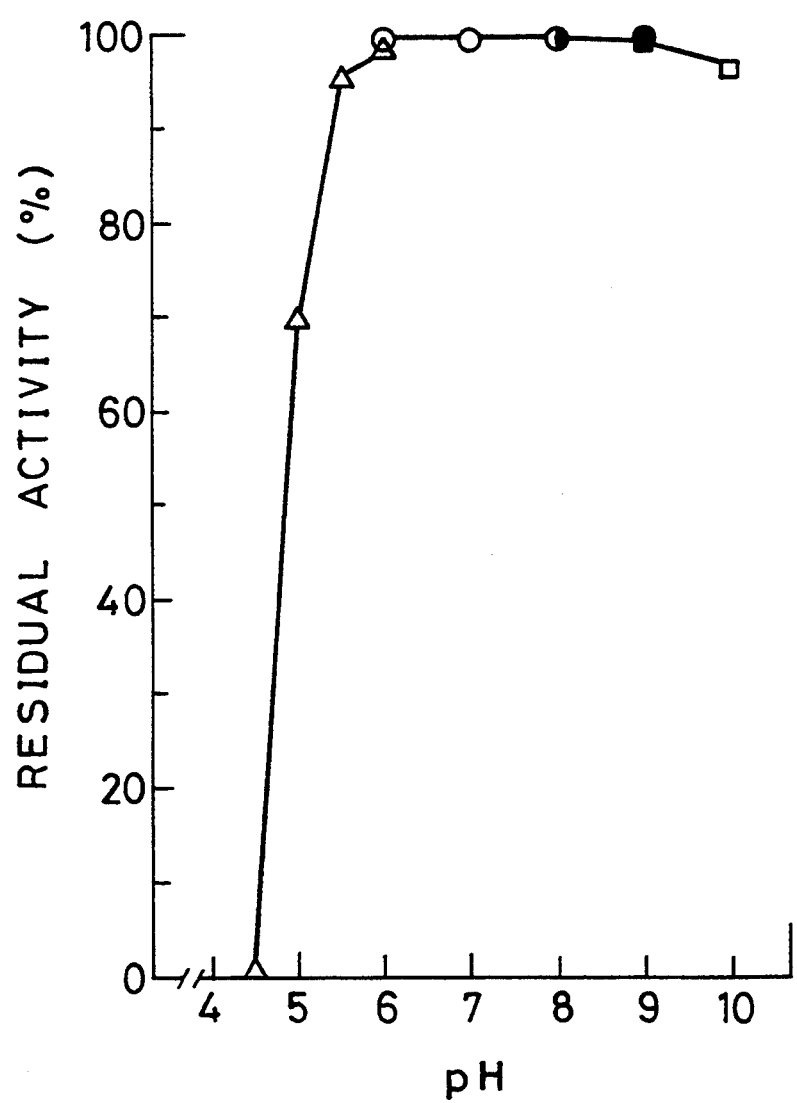
FIG. 2 is a graph showing the stable pH range of the acyl-carnitine esterase according to the present invention.

In the graph of FIG. 2, the marks $\triangle$, $\bigcirc$, $\bullet$ and $\square$ correspond to acetate buffer solution, phosphate buffer solution, tris-HCl buffer solution and glycine/NaOH buffer solution, respectively.

Figure 3:
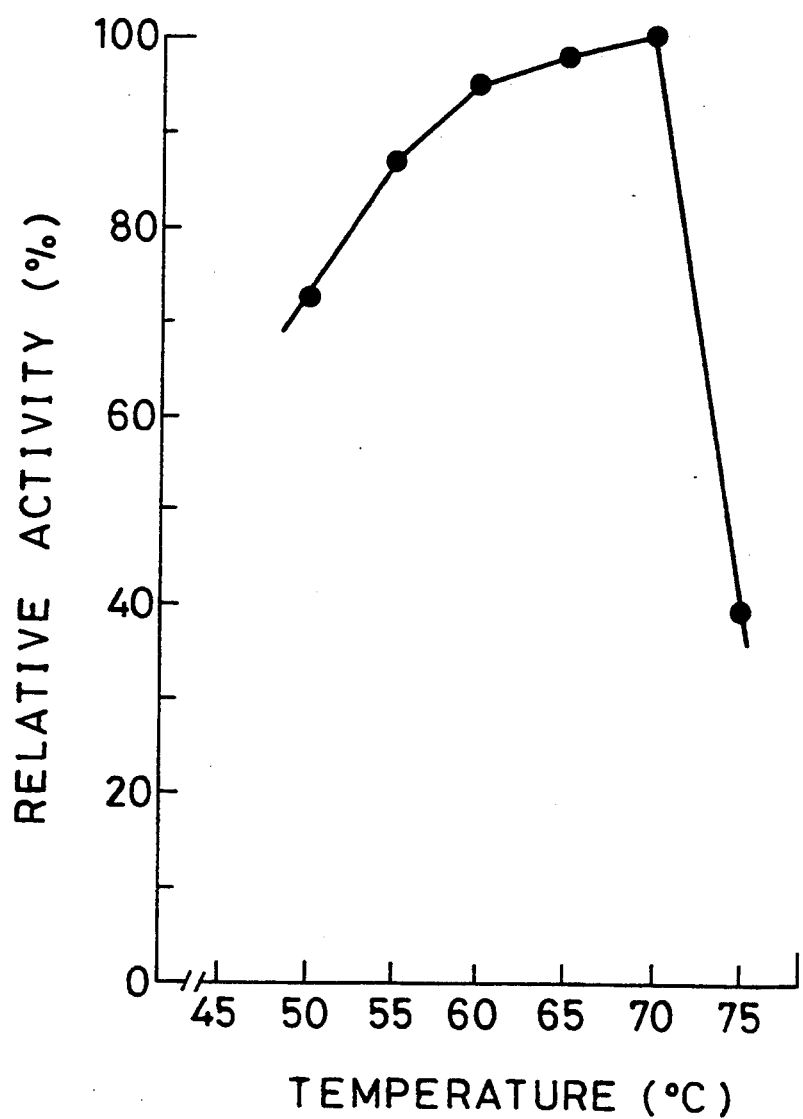
FIG. 3 is a graph showing the optimum temperature of the acyl-carnitine esterase according to the present invention.

8. Optimum temperature:

Using a 0.5 mM octanoyl-L-carnitine solution of pH 8.0 in 100 mM tris-HCl buffer solution, an enzymatic hydrolysis reaction was carried out at 50°, 55°, 60°, 65°, 70° and 75° C. each for 10 mins., whereupon the amount of L-carnitine formed was determined. The results of analysis were as illustrated on the graph of FIG. 3, which shows the maximum activity at 70° C.

Figure 4:
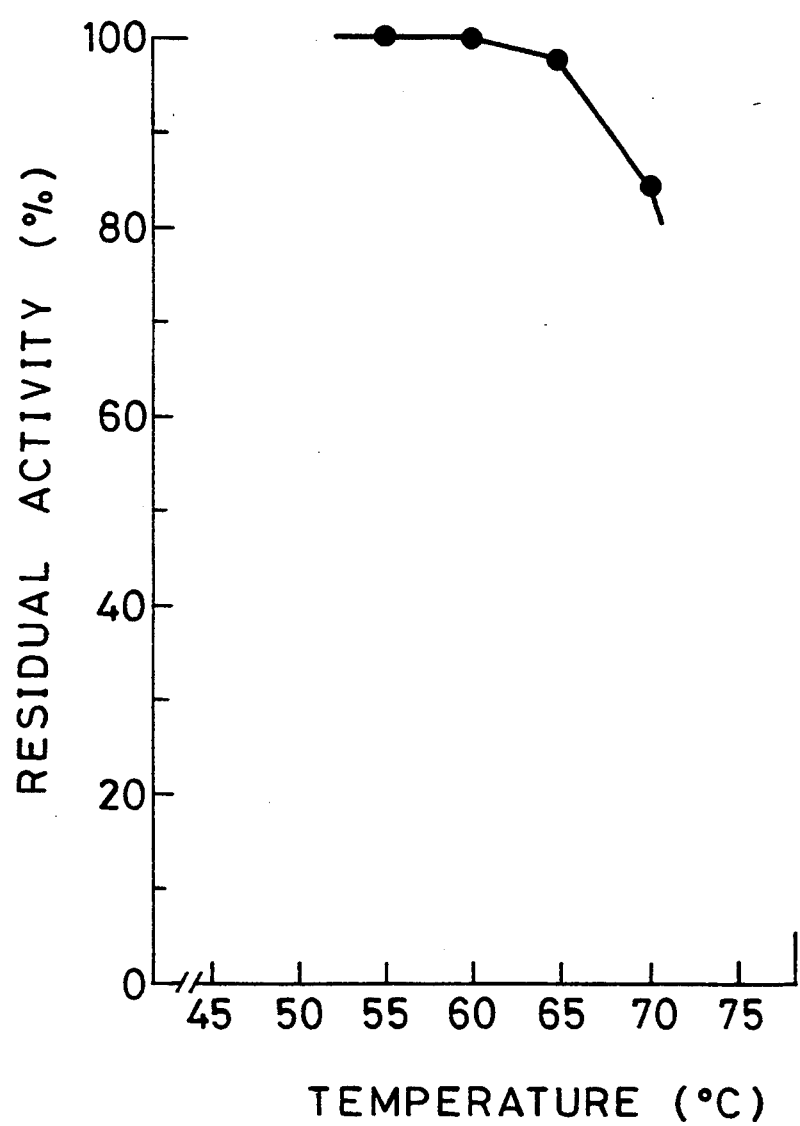
FIG. 4 is a graph showing the heat stability of the acyl-carnitine esterase according to the present invention.

9. Heat stability:

A set of solutions of the esterase according to the present invention were prepared using 100 mM tris-HCl buffer solution (pH 8.0) so that each of the solutions had a concentration of the esterase of 0.10 Unit/ml. Each of these solutions was heat treated respectively at 55°, 60°, 65° or 70° C. for 30 mins., whereupon it was examined for its residual enzymatic activity. The results are shown in FIG. 4, which shows that the esterase is stable up to 60° C.

10. Assay method of acyl-carnitine esterase:

a. Reaction Mixture:
tris-HCl buffer solution (pH 8.0): 100 mM
octanoyl-L-carnitine: 0.5 mM b. Procedure:

1 ml of the above reaction solution is placed in a small test tube and is incubated at 37° C. for 5 mins. and 0.05 ml of esterase solution is then added thereto, suitably diluted, and the resulting solution is incubated at 37° C. for 15 mins., whereupon the reaction is terminated at once by transferring the test tube into a boiling water bath and subjecting the solution to incubation for 15 seconds to prepare a sample solution to be inspected. The amount of L-carnitine produced is determined according to the L-carnitine determination method described hereinafter to assess the activity of the acyl-carnitine esterase.

c. Calculation equation:

$$\text{Unit/ml} = \frac{A_1 - A_0}{21.7} \times \frac{1}{15} \times \frac{3.05}{0.05} \times \frac{1.05}{0.05} \times Z$$

(in which Z is the dilution factor and the numerals 21.7 and 15 correspond each to the molecular extinction coefficient in cm$^2$/$\mu$mol and the reaction time in minutes, respectively).

d. Method for analyzing L-carnitine (designated hereinafter as analysis method A):

(1) Composition of the reaction solution:

| Tris-HCl buffer solution (pH 9.0) | 100 mM |
| --- | --- |
| NAD+ | 1 mM |
| Diaphorase (of Toyo Jozo Co. Ltd.) | 5 Units |
| L-carnitine dehydrogenase (originating from *Alcalicignes sp.* No. 981, supplied by Toyo Jozo) | 15 Units |
| KCl | 100 mM |
| NBT (of Wako Pure Chemical Ind.) | 0.025% |
| Polyoxyethylene (20) sorbitan-monooleate (of Wako Pure Chemical Ind.) | 0.5% |

(2) Procedure:

1 ml of the above reaction solution is placed in a small test tube and is incubated at 37° C. for 5 mins. and then there is added thereto 0.05 ml of the esterase solution to be examined and the resulting solution is incubated for 2 mins., whereupon 2 ml of 0.1N aq. HCl is added thereto and the solutio is examined for $A_{550\,nm}$ to obtain the absorbance $A_1$. Also the absorbance $A_0$ for the blank test solution without addition of the esterase solution is determined in the same way.

(3) Calculation equation:

$$n\,\text{mole/ml} = \frac{A_1 - A_0}{21.7} \times \frac{3.05}{0.05}$$

As described above, the acyl-carnitine esterase according to the present invention exhibits an enzymatic action not only for the acyl-L-carnitines of medium-to-long chain lengths, but also for short-chain acyl-L-carnitines for which the conventional acyl-carnitine esterase are ineffective. Therefore, acyl-L-carnitines contained in a sample solution of the substances to be examined, such as human serum and so on, can be determined by subjecting the sample solution in enzymatic hydrolysis with the acyl-carnitine esterase according to the present invention which exhibits a substrate-specificity not only for acyl-L-carnitines of medium-to-long-chain acyl-carnitine but also for short-chain acyl-carnitines inclusive of acetyl-L-carnitine and propionyl-L-carnitine, and then determining the amount of the fatty acids or L-carnitine thus formed, by an analytical technique known per se.

If there is free L-carnitine in the sample solution in addition to the acyl-L-carnitines, the analysis of the acyl-carnitines may be effected by, for example, determining preliminarily the amount of free L-carnitine by the analysis technique described hereinafter; decomposing the free L-carnitine with a reducing coenzyme such as a system in which NADH is converted into oxidized form, and heating the reaction mixture, whereupon the acyl-L-carnitines are analyzed; or converting all the acyl-L-carnitines into free L-carnitine using the esterase according to the present invention and comparing the total L-carnitine with that originally existing, by a known analytical technique.

No special reaction conditions are required for the acyl-L-carnitines in the sample solution with the acyl-carnitine esterase according to the present invention, so long as sufficient hydrolysis of the acyl-L-carnitines in the sample solution is attainable. But it is recommended to effect the reaction by incubating the esterase-inoculated sample mixture at a temperature of, for example, 37° C. for a time interval of, for example, 5–30 mins. The enzymatic hydrolysis reaction may preferably be terminated by heating the reaction solution to a temperature above 80° C.

By the enzymatic hydrolysis effected as above, the corresponding fatty acid and L-carnitine are liberated from the acyl-L-carnitine. Therefore, the amount of the acyl-L-carnitine can be determined by quantitatively analyzing either the amount of the free fatty acid or that of L-carnitine.

The quantitative determination of the fatty acid can be effected by an analysis technique known per se. Ordinary analysis techniques include, for example, liquid chromatography and gas chromatography. The known techniques for quantitatively determining L-carnitine include, for example, a colorimetric method using a carnitine acetyl-transferase (CAT), acetyl-CoA and 5,5'-dithio-bis-nitrobenzoic acid (DTNB) reported in "J. Biol. Chem.", 238, 2509 (1963) and "J. Lipid Research", 5, 184–187 (1964); a method with radioisotopes using $^{14}$C- or $^{3}$H-labelled acetyl-CoA and CAT reported in "Clin. Chim. Acta", 37, 235–243 (1972) and "J. Lipid Research", 17, 277–281 (1976); a carnitine dehydrogenase method using a carnitine dehydrogenase NAD+ as reported in "Europoean J. Biochem.", 6, 196–201 (1968); and a fluorimetric method using acetyl-CoA, CAT and N-[p-[2-benzimidasol-yl)-phenyl]-maleimide (BIPM) as reported in the 61st year's Research Report of Institute of Neuropathy of the Ministry of Health and Welfare, Japan, 315–318 (1986). Among these, the carnitine dehydrogenase method is recommended. This method comprises subjecting the sample solution to the action of a reagent containing an L-carnitine dehydrogenase and a member of the nicotinamide adenine dinucleotide group (NAD group) or a thio member of the nicotinamide adenine dinucleotide group (thio-NAD group) with, if necessary, a non-ionic detergent, and determining the amount of the member of the reduced NAD group or the reduced thio-NAD group formed thereby. For the NAD group, nicotinamide adenine dinucleotide (NAD), acetylpyridine adenine dinucleotide (acetyl-NAD), nicotinamide hypoxanthine dinucleotide (deamino-NAD) and so on may be used. For the thio-NAD group, there may be used, for example, thionicotinamide adenine dinucleotide, thionicotinamide hypoxanthine dinucleotide and so on.

While the analysis of the reduced NAD group or reduced thio-NAD group formed by the reaction can be effected by a direct determination of the absorbance of the reacted sample solution, it is preferable to determine it by converting the reaction system into a formazan-forming system represented by the following reactions:

(1) L-carnitine dehydrogenase (LCD) reaction system

(2) Conversion reaction system

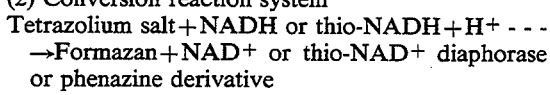

The L-carnitine dehydrogenase to be employed according to the present invention is a known enzyme and it is here recommend to use a bacteria-originated dehydrogenase produced by an L-carnitine-dehydrogenase-producing bacterium. Examples of such L-carnitine-dehydrogenase-producing bacteria are those of the genus Pseudomonas such as *Pseudomonas aeruginosa* IFO 13130, *Pseudomonas putilda* B-0781 (FERMP-5664) and *Pseudomonas putida* IF 03738, those of the genus Xanthomonas such as *Xanthomonas tranlucens* IFO 13558 and so on. The bacteria-originated L-carnitine dehydrogenase can be obtained according to the procedures described in "European J Biochem", 6, 196–201 (1968), ibid. 10, 56–60 (1969), "Agric. Biol. Chem.", 52 (1), 249–250 (1988), by cultivating the bacteria, collecting the dehydrogenase from the cultured product and purifying it. They can be obtained also by means of a gene recombination technique by producing a recombinant host-cell having the L-carnitine-dehydrogenase-producing gene of a bacterium mentioned above, cultivating it and collecting the dehydrogenase produced (see for example "Agric. Biol. Chem.", 52 (3), 851–852 (1988)). The bacterium *Alcaligene sp.* No. 981 also produces an L-carnitine dehydrogenase. It is preferred to carry out the culture in a culture medium containing carnitine.

In the analysis methods proposed above, an electron transfer agent, namely, an agent capable of effecting the conversion from tetrazolium salt, NAD-group (or thio-NAD group) and H+ into formazan and NAD+ (or thio-NAD+), such as diaphorase, a phenazine derivative or so on, is used.

Diaphorase is a known enzyme and is commercially available.

As the phenazine derivatives, there may be used, for example, phenazine methosulfate, meldola's blue and methoxyphenazine methosulphate.

As the tetrazolium salt to be employed in these analysis methods, there may be used, for example, 3,3'-(3,3'-dimethoxy-4,4'-biphenylene)-bis-[2-(p-nitrophenyl)-5-phenyltetrazolium chloride], commonly called nitrotetrazolium (NBT); 3,3'-(3,3'-dimethoxy-4,4'-biphenylene)-bis[2,5-bis(p-nitrophenyl)-tetrazolium chloride]; 3,3'-(3,3'-dimethoxy-4,4'-biphenylene)-bis[2,5-diphenyl-tetrazolium chloride]; 2-(p-nitrophenyl)-3-(p-iodophenyl)-5-phenyl-tetrazolium chloride (INT); 3-(4,5-dimethyl-2-thiazolyl)-2,5-diphenyl-tetrazolium chloride (4,5-MTT); 3-(4,5-dimethyl-2- triazolyl)-2,4-diphenyltetrazolium chloride (MTT); 2,2'-5,5'-tetra-(p-nitrophenyl)-3,3'-(3-dimethoxy-4-diphenylene)-ditetrazolium chloride (TNBT); 2,3,5-triphenyl-tetrazolium chloride (TT); and neotetrazolium chloride (NT).

For the non-ionic detergent to be added to the reaction system, those water soluble ones which have HLB values above 10 and exhibit no negative influence disturbing the reaction are employed. It is preferable to employ a non-ionic detergent having HLB values in the range from about 11 to 17. Examples of such non-ionic detergents include polyoxyethylene alkyl ethers such as polyoxyethylene oleyl ether, polyethylene cetyl ether, polyoxyethylene stearly ether, polyoxyethylene lauryl ether, polyoxyethylene hexadecyl ether and polyoxyethylene tridecyl ether; polyoxyethylene alkaryl ethers such as polyoxyethylene nonylphenyl ether and polyoxyethylene octylphenyl ether; polyoxyethylene polyoxypropylene ethers such as polyoxyethylene polyoxypropylene cetyl ethers etc.; polyoxyethylene alkyl esters, such as, polyoxyethylene monostearate, polyoxyethylene monolaurate and polyoxyethylene monooleate; sorbitan derivatives such as sorbitan monolaurate, sorbitan monopalmitate, sorbitan monostearate, sorbitan tristearate, sorbitan monolaurate, sorbitan sesquioleate and sorbitan trioleate; glycerin propylene glycol fatty acid esters such as glycerin monostearate, polypylene glycol monostearate and glycerin monooleate; polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate and polyoxyethylene sorbitan trioleate; polyoxyethylene sorbitol fatty acid esters such as polyoxyethylene sorbitol monolaurate, polyoxyethylene sorbitol tetraoleate and polyoxyethylenesorbitol hexastearate; polyoxyethyleneglycerin fatty acid esters such as polyoxyethylene glycerin monostearate etc.; polyoxyethylene alkylamine such as polyoxyethylene stearylamine etc.; polyoxyethyleneamides such as polyoxyethylene stearylamide etc.; fatty acid alkanolamides such as lauric acid dimethanolamide, coconut oil fatty acid diethanolamide and so on; polyoxyethylene castor oil derivatives such as polyoxyethylene-hydrogenated castor oil derivatives etc.; primary alcohol ethoxylates such as Adekanol (a product of Asahi Denka Kogyo) etc.; secondary alcohol ethoxylates such as Adekatol (a product of Asahi Denka Kogyo and polyoxypropylene polyoxyethylene ethers of ethylenediamide such as Tetronic (a product of Asahi Denka Kogyo). Among these, polyoxyethylene polyoxypropylene ethers such as Pronic F-68 (a product of Asahi Denka Kogyo); polyoxyethylene sorbitan fatty acid esters such as polyoxyethylene (20) sorbitan monooleate (a product of Wako Pure Chemical Ind.); sorbitan fatty acid esters; and secondary alcohol ethyoxylates such as Adekatol (Asahi Denka Kogyo) are preferred. These non-ionic detergents may be employed alone or in combination.

The concentration of the enzyme and that of the reagents to be employed in carrying out the quantitative determination of L-carnitine in the sample solution may, in general, be selected in the ranges given below to conduct the contemplated reaction:

| Component | Concentration |
|---|---|
| L-carnitine dehydrogenase | 1–30 U/ml |

-continued

| Component | Concentration |
|---|---|
| $NAD^+$ (or thio-$NAD^+$) | 0.1–5 mM |
| Diaphorase | 0.5–50 U/ml |
| Tetrazolium salt | 0.01–0.1% |
| Non-ionic detergent | 0.1–5% |

The enzymes and other requisite reagents may be stored as an aqueous solution in a separate system or in a combination system composed of two or more of the components or as a dry powder. It is advantageous to employ breeze drying for storing them in the form of dry powder. In order to assure stable storage of the enzymes and other requisite reagents, it is preferred to store each of them either alone or in combination with other components having no negative influence on stability. For example, it is not preferred to store the L-dehydrogenase in combination with the non-ionic detergent, the $NAD^+$ or thio-$NAD^+$ in combination with the tetrazolium salt, the electron transfer agent in combination with the tetrazolium salt and the non-ionic detergent in combination with the tetrazolium salt in one single system for long-term storage.

The reaction of the reaction systems for the quantitative analysis of the acyl-L-carnitines mentioned above can be effected usually at a temperature around 37° C. for at least 1 min. If the reaction produces any turbidity in the reaction mixture, an additive such as KCl, NaCl, etc., may be incorporated in the reaction system for avoiding the occurrence of such turbidity.

The amount of L-carnitine in the reaction system can be determined by colorimetry, using light of a wavelength around the specific absorption band of the formazan formed by the reaction, namely, 500–550 nm.

It is also possible to carry out the analysis of L-carnitine by reacting with the sample solution containing the L-carnitine a reagent containing an L-carnitine dehydrogenase and a combination of either (1) a NAD group with a reduced thio-NAD group or (2) a thio-NAD group with a reduced NAD group, for performing a cycling reaction expressed by the reaction scheme

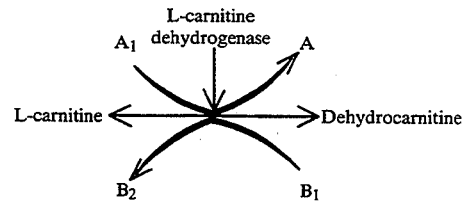

in which $A_1$ denotes the NAD group or thio-NAD group, $A_2$ denotes the corresponding reduced form of $A_1$, $B_1$ represents the reduced thio-NAD group when $A_1$ denotes an NAD group or represents the reduced-NAD group when $A_1$ denotes a thio-NAD group, and $B_2$ represents the corresponding oxidized product of $B_1$, and then determining the amount of $B_1$ consumed during the cycling reaction or the amount of $A_2$ formed during the cycling reaction. This reaction system is characterized by a very high sensitivity and is particularly preferred.

In this reaction system, it is necessary that at least one of the combinations be a thio-coenzyme; for example. $A_1$ should be NAD when $B_1$ is thio-NADH, and $A_1$ should be thio-NAD when $B_1$ is NADH.

It is necessary that the amount of $A_1$ and $B_1$ be in molar excess of the amount of L-carnitine in the sample solution and also in excess as compared with the Km value of the L-carnitine dehydrogenase for either of $A_1$ and $B_1$; and it is preferred in particular that the amount of $A_1$ and of $B_1$ be about 20–10,000 times the amount of L-carnitine.

It is preferred, in the analytical reagent for determining the amount of L-carnitine in the above reaction system, that the concentration of $A_1$ and of $B_1$ being the range 0.02–100 mM, especially in the range 0.05 to 30 mM. The concentration of L-carnitine dehydrogenase should preferably be in the range 5–200 Units/l, in particular, 10–150 U/ml, although higher concentration can be used.

The L-carnitine dehydrogenase used in preparing the analysis reagent for determining the amount of L-carnitine, should have reactivity to the substrate, namely, L-carnitine, and may be employed in combination with a coenzyme such as an NAD (preferably NAD or thio-NAD). Such reactivity can be confirmed using the combination of such coenzyme with the substrate. For example, it has been confirmed that, when using L-carnitine as the substrate and thio-NAD as the coenzyme in 100 mM tris-HCl buffer solution (pH 9.0), the L-carnitine dehydrogenase produced from *Alcaligenes sp.* No. 981 (from Toyo Jozo) exhibits an enzymatic activity of about 15% relative to the activity when using NAD as the coenzyme. The Km values for L-carnitine, NAD and thio-NAD were found to be 9.3 mM, 0.14 mM and 0.49 mM respectively, under the same conditions.

For the reaction solution composition, it is recommended to select the combination of the two coenzymes with regard to the balance of their activities relative to each other for each specific L-carnitine dehydrogenase employed and to select the pH so as to cause the reaction rate proportion of forward/reverse reaction to approach unity as closely as possible.

In the analytical processes according to the present invention, a single L-carnitine hydrogenase can be employed or a combination of a plurality thereof.

The quantitative determination of the amount of L-carnitine contained in the reacted sample solution using the analysis reagent for determining L-carnitine for the reaction system described above can be performed by, for example, adding to the reagent containing the above three essential components the reacted sample solution in an amount of 0.01–0.5 ml and causing the enzymatic reaction at a temperature of about 37° C. and determining the amount of $A_2$ formed or the amount of $B_1$ consumed during the reaction at two points of time spaced by a predetermined time interval, for example, a time interval of 1 min., e.g., between 3 mins. and 4 mins. from the start of the reaction, or a time interval of 5 mins., e.g., between 3 mins. and 8 mins. from the start of the reaction, by means of spectrophotometry by observing the change in the absorbance during such time interval at the wavelength corresponding to the specific absorption band for the components. It is also possible to observe the change in the absorbance during the reaction by terminating the reaction after a predetermined time interval, such as after 10 mins., from the start of the reaction. Specifically, the amount of $A_2$ formed may be determined by measuring the increase in the absorbance at 400 nm (molar extinction coefficient $=11,200 M^{-1} cm^{-1}$; Cf. "Methods in Enzymology", Vol 55, 261 (1979)), when $A_2$ is thio-NAD and $B_1$ is NADH, or by determining the consumption of $B_1$ by measuring the decrease in the absorbance at a wavelength of 340 nm (molar extinction coefficient $=6220 M^{-1} cm^{-1}$) and comparing the detected value with the preliminarily obtained values for known concentrations of L-carnitine, in order to perform a real time assay of the amount of L-carnitine in the substance to be examined.

Since the above analytical method relies on the enzymatic cycling reaction of L-carnitine itself in the sample solution, it suffers little from any influence of the coexisting substances in the sample solution, so that it is permissible to dispense with a blank determination of the sample solution, resulting in a convenient and simple procedure.

In this reaction system, it is also possible to perform the determination of $A_2$ or $B_1$ by means of other known methods for determining enzymes instead of the direct measurement of the absorbance.

The acyl-carnitine esterase according to the present invention can provide a way of determining the short-chain acyl-L-carnitine in the sample solution by a combined use thereof with the prior art acyl-carnitine esterase, since the acyl-carnitine esterase according to the present invention has an enzymatic activity also for short-chain acyl-L-carnitines, namely, acetyl-L-carnitine and propionyl-L-carnitine.

Thus, the present invention provides another process for determining the amount of the short-chain acyl-L-carnitines in a specimen to be examined, which comprises the steps of (a) subjecting a sample of said specimen to enzymatic hydrolysis with an acyl-carnitine esterase which has no enzymatic activity for acetyl-L-carnitine and propionyl-L-carnitine but which has substrate specificity for acyl-L-carnitines of medium chain lengths to long chain lengths and catalyzes the hydrolysis of one mole of each acyl-L-carnitine of said medium chain lengths to long chain lengths with one mole of water to form one mole of the corresponding fatty acid and one mole of L-carnitine (which esterase is denoted hereinafter as long chain acyl-carnitine esterase) and then determining the amount of the fatty acid and/or L-carnitine thus formed, by an analysis technique known per se.

(b) subjecting another parallel sample of said specimen to enzymatic hydrolysis with another acyl-carnitine esterase which has substrate specificity for acyl-carnitines including short chain acyl-carnitines comprising acyl-L-carnitines including acetyl-L-carnitine and propionyl-L-carnitine and catalyzes the hydrolysis of one mole of each of the acyl-L-carnitines with one mole of water to form one mole of the corresponding fatty acid and one mole of L-carnitine, and then determining the amount of the fatty acid or L-carnitine thus formed, by an analysis technique known per se, and (c) estimating the difference of the analytical values between the above process steps (a) and (b).

Although various long chain acyl-carnitine esterases can be employed in the process step (a) of the above analytical method, it is recommended to employ a rat-originated acyl-carnitine esterase.

The procedures in the above process steps (a) and (b) are essentially the same. The difference in the determined values between the process steps (a) and (b) corresponds to the amount of the short-chain acyl-L-carnitines in the sample solution.

The short-chain acyl-L-carnitines in a specimen to be examined can be analyzed by a further alternative process according to the present invention, which comprises the steps of ($a_1$) subjecting a sample of said specimen to the action of a long-chain acyl-carnitine esterase, and then subjecting the resulting reacted sample mixture to the action of a combination of an L-carnitine dehydrogenase with a coenzyme ($A_1$ denotes an NAD or a thio-NAD) to convert $A_1$ into its reduced form $A_2$, and treating the resulting sample mixture so as to cause decomposition of the resulting $A_2$, ($b_1$) subjecting the resulting reacted sample mixture to the action of an acyl-carnitine esterase which has substrate specificity for the short-chain acyl-carnitines consisting of acetyl-L-carnitine and propionyl-L-carnitine and catalyzes the hydrolysis of one mole of each of the short-chain acyl-L-carnitines with one mole of water to form one mole of the corresponding fatty acid and one mole of L-carnitine, and determining the amount of the fatty acids or L-carnitine thus formed, by an analysis technique known per se.

The enzymatic reaction in the process step ($a_1$) can be carried out in the same manner as that of (a) of the foregoing analysis method. The decomposition of $A_2$ in the process step ($a_1$) of this analysis method is carried out by warming or heating the reacted sample mixture under an acidic condition at a temperature of 37° C. or higher, whereby all the L-carnitine, namely, that derived from the medium- to long-chain acyl-L-carnitines plus that existing originally, is removed from the reaction system by decomposition. Thus, upon the decomposition of $A_2$, the sample mixture now contains only the lower-L-carnitines, whereby the amount of the short-chain acyl-L-carnitines can be determined by the process step ($b_1$) which is essentially the same as (b) in the first analysis method.

The acyl-carnitine esterase according to the present invention has a distinctive feature in that it has substrate-specificity also for the short-chain acyl-L-carnitines including acetyl-L-carnitine and propionyl-L-carnitine, for which the conventional acyl-carnitine esterases have no substrate specificity. In addition, the acyl-carnitine esterase according to the present invention has a lower Km value for various acyl-L-carnitines and is superior also as to stability. By making use of these superior features of the acyl-carnitine esterase according to the present invention, advantageous and convenient ways for the determination of acyl-carnitines are available.

The present invention proposes also an advantageous process for the production of such acyl-carnitine esterase by making use of the excellent heat stability of the esterase, permitting easier purification with simple and economical large-scale production by aerobic cultivation.

DETAILED DESCRIPTION OF PREFERRED EMBODIMENTS

Below, the present invention will further be described specifically by way of examples. It is to be understood that it is not intended by these specific examples to impose on the present invention any restriction.

Example 1

Culture of *Alcaligenes sp.* No. 981

Aliquots of 100 ml of a liquid culture medium (pH 7.0) containing 0.2% of $KH_2HO_4$, 0.4% of $K_2HPO_4$, 0.05% of $MgSO_4.7H_2O$, 0.02% of $FeSO_4.7H_2O$, 0.02% of $MnSO_4.nH_2O$ and 0.1% of yeast extract (a product of Kyokuto Seiyaku) were charged in five Erlenmeyer flasks of 500 ml capacity and were sterilized by heating at 120° C. for 20 mins. 5 ml preliminarily sterilized 10% octanoyl-DL-carnitine (a product of Sigma) were added to each of the flasks under aseptic conditions, which were then inoculated with a small amount of *Alcaligenes sp.* No. 981 and the mixture was cultivated at 28° C. for 72 hours in a shaking cultivator with shaking of 120 r.p.m. A total of 470 ml of the cultured product liquor was obtained.

Example 2

Separation and Purification of Acyl-carnitine Esterase According to the Invention 470 ml of the cultured product liquor was subjected to centrifugation to collect the bacterial cells, which were suspended in 50 ml of 100 mM tris-buffer solution (pH 8.0). This suspension was homogenized using an ultrasonic disintegrator (made by Kubota), whereupon it was subjected to centrifugation at 15,000 r.p.m. for 10 mins. to obtain 45 ml of a supernatant (0.3 U/ml). This crude enzyme solution was heat treated at 60° C. for 30 mins., whereupon it was again centrifuged at 15,000 r.p.m. to obtain 44 ml of a supernatant (0.3 U/ml). The resulting enzyme solution was passed through a gel filtration column charged with 20 ml of DEAE-Sepharose CL-6B (made by Pharmacia) which had been buffered with 50 mM tris-HCl buffer solutio (pH 8.0), whereupon 100 ml of 5 mM tris-buffer solution (pH 8.0) containing 0.1M KCl were passed through the thus-charged column, before the column was eluted with 50 mM Tris-HCl buffer solution (pH 8.0) containing 0.25M KCl. By this elution, 25 ml of an enzyme solution (0.47 U/ml) was obtained. This enzyme solution was dialyzed overnight at 5° C. against 10 liters of 50 mM tris-HCl buffer solution (pH 8.0), whereby 28 ml of an enzyme solutio (0.41 U/ml; yield=85%) was obtained. 20 ml of this enzyme solution was freeze-dried, whereby 80 mg of pulverulent product (0.1 U/mg) was obtained.

Reference Example 1

Culture of *Alcaligenes sp.* No. 981 for the Production of L-carnitine Dehydrogenase 100 ml of liquid culture medium (pH 7.0) containing 3% of DL-carnitine chloride (a product of Sigma), 0.2% of $KH_2HO_4$, 0.4% of $K_2HPO_4$, 0.05% of $MgSO_4.7H_2O$, 0.002% of $FeSO_4.7H_2O$, 0.001% of $MnSO_4.nH_2O$ was charged in a 500 ml Erlenmeyer flask and sterilized by heating at 120° C. for 20 mins. This culture medium was inoculated with a small amount of *Alcaligenes sp.* No. 981 and the mixture was cultivated in a shaking cultivator at a shaking rate of 120 r.p.m. at 28° C. for 40 hours to obtain 95 ml of a culture mother liquor (enzymatic activity=1.2 U/ml).

On the other hand, 20 liters of liquid culture medium (pH 7.0) containing 3% of DL-carnitine chloride (a product of Sigma), 0.1% of a yeast extract (a product of Kyokuto Seiyaku), 0.054% of $KH_2HO_4$, 0.746% of $K_2HPO_4$, 0.05% of $MgSO_4.7H_2O$, 0.002% of $CaCl_2.2$-

$H_2O$, 0.002% of $FeSO_4.7H_2O$, 0.002% of $MnSO_4.nH_2O$ and 1 ml/l of Disfoam CB442 (a product of Nippon Oils and Fats) was charged in a 30 l jar fermenter and was sterilized by heating. This liquid culture medium was inoculated with 90 ml of the culture mother liquor obtained above and the mixture was subjected to aeration cultivation under the conditions of a culture temperature of 28° C., an aeration rate of 20 liter/min., a fermenter inner pressure of 0.4 kg/cm$^2$, an agitation rate of 200 r.p.m. and a culture duration of 27 hours, whereby 19 liters of cultured product (enzymatic activity=3.0 U/ml) was obtained.

Reference Example 2

Separation and Purification of L-carnitine Dehydrogenase 90 liters of the cultured product obtained in Reference Example 1 were subjected to centrifugation for collecting the bacterial cells. The collected bacterial cells were subjected to a solubilization treatment at 37° C. for 1 hour by adding thereto 4 liters of a 40 mM tris-HCl buffer solution (pH 8.0) containing 0.1% of lysozyme and 15 mM of ethylenediamine tetraacetic acid disodium salt (EDTA.2Na). The treated mixture was subjected to centrifugation to obtain 4,500 ml of a supernatant (having a specific enzymatic activity of 10.3 U/ml). In this supernatant, 1,100 g of ammonium sulfate was dissolved and the thereby formed precipitate was removed by centrifugation, whereupon 700 g of ammonium sulfate was again dissolved in the resulting supernatant. The thus-treated supernatant was then subjected to centrifugation to obtain a precipitate, which was dissolved in 500 ml of 40 mM tris-HCl buffer solution (pH 8.0) and this solution (which has a specific enzymatic activity of 84.1 U/ml) was dialyzed against 10 liters of 40 mM tris-HCl buffer solutio (pH 8.0). The dialyzed enzyme solution was passed through a gel filtration column packed with 200 ml of DEAE-Sepharose CL-6B (a product of Pharmacia) which had been buffered with 40 mM tris-HCl buffer solution (pH 8.0), followed by a displacement of the filter bed by passing therethrough 1 liter of a 40 mM tris-HCl solution (pH 8.0) containing 0.1M KCl, whereupon the column was eluted using 40 mM tris-HCl buffer solution (pH 8.0) containing 0.3M KCl to obtain 300 ml of an enzyme solution (having a specific enzymatic activity of 12.5 U/ml). This enzyme solution was dialyzed against 10 liters of 40 mM tris-HCl buffer solution (pH 8.0). The dialyzed enzyme solution was passed through a column packed with 100 ml of hydroxyapatite (a product of KOKEN) which had been buffered with 40 mM tris-HCl buffer solution followed by a displacement procedure by passing therethrough 200 ml of 40 mM tris-HCl buffer solution (pH 8.0), whereupon the column was eluted with 800 ml of 2 mM phosphate buffer solution (pH 7.0) to obtain 100 ml of an enzyme solution (specific enzymatic activity=331 U/ml). This enzyme solution was dialyzed against 5 liters of phosphate buffer solution (pH 7.5), whereby 95 ml of a dialyzed enzyme solution was obtained (specific enzymatic activity=331 U/ml; recovery yield=67.8%).

The NADH-oxidase activity in this purified L-carnitine dehydrogenase was found to be not higher than 0.0001 U/ml.

The properties of the L-carnitine dehydrogenase obtained as above were as given below:

1. Enzymatic activity:

It catalyzes at least the reaction of L-carnitine with NAD to form 3-dehydrocarnitine and NADH, as illustrated in the following reaction scheme:

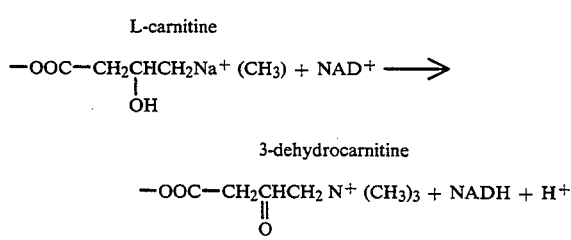

2. Substrate specificity:

| Substrate | Relative Specificity % |
|---|---|
| L-carnitine | 100 |
| Choline | 0 |
| Glycinebetaine | 0 |
| Glucose | 0 |
| Lysine | 0 |

3. Molecular weight: 51,000±6,000

The molecular weight was determined by molecular sieve chromatography using TSK Gel G3000 SW (a product of Toso) on a column of 7.5×60 cm using an eluent consisting of a 0.1M phosphate buffer solution (pH 7.0) containing 0.2M NaCl with the use of the following standard molecular weight markers supplied by Oriental Kobo:

| Molecular Weight | Compound |
|---|---|
| 12,000 | Cytochrome C |
| 32,000 | Adenylate kinase |
| 67,000 | Enolase |
| 142,000 | Lactate dehydrogenase |
| 290,000 | Glutamate dehydrogenase |

4. Isoelectric point: pH 5.3±0.6

The isoelectric point was determined by isoelectric focussing using a carrier ampholyte under a constant voltage of 700 V for 40 hours, whereupon the solution was subjected to fractionation and each fraction was examined for enzymatic activity.

5. Km value:

Km value for NAD+ was determined by varying the concentration of the NAD+ in a reaction solution containing 100 mM tris-HCl buffer solution (pH 9.0). 5 units of diaphorase (a product of Toyo Jozo), 0.025% of NBT (a product of Wako Pure Chemical Ind.), 1% of Tween 80 (a product of Wako Pure Chemical Ind.) and 50 mM L-carnitine, whereby a value of 0.141 mM was obtained.

On the other hand, the Km value for L-carnitine was determined by varying the concentration of L-carnitine in the above reaction solution in which 50 mM of L-carnitine was replaced by 1 mM NAD+, whereby a value of 9.3 mM is obtained.

6. Heat stability:

A solution of this esterase (1.00 U/ml) was prepared using 20 mM tris-HCl buffer solution (pH 8.0). This solution was heat treated for 1 hour, whereupon the residual enzymatic activity was determined in accordance with the method for determining enzymatic activity described hereinafter, which showed that the enzymatic activity was stable at least up to a temperature of 45° C.

7. Optimum temperature:

Using 100 mM tris-HCl buffer solution (pH 9.0), storage stability at 5° C. for two weeks was observed. The L-carnitine dehydrogenases obtained from the three strains of L-carnitine-dehydrogenase-producing known bacteria cited previously showed residual enzymatic activities after one week of about 53–40% which was decreased to below 45% after two weeks. In particular, the enzyme produced from Pseudomonas aeruginosa IFO 13130 was the most unstable and exhibited a residual activity of only 41%. In contrast thereto, the L-carnitine dehydrogenase obtained from the bacterium according to the present invention exhibited a residual enzymatic activity of 96% after one week and 82% after two weeks, showing that it has considerably higher stability as compared with the conventional enzymes derived from the L-carnitine-dehydrogenase-producing known bacteria. When 0.05 mM NAD+ was caused to coexist in this storage stability test, the residual enzymatic activity was found to be 99.7% after one week and 95.1% after two weeks, which is even higher than the above, suggesting a stabilizing effect of NAD+.

8. Method for determining the enzymatic activity of the L-carnitine dehydrogenase:

(a) Composition of the reaction solution:

| Tris-HCl buffer solution (pH 8.0) | 50 mM |
|---|---|
| NAD+ | 1 mM |
| Diaphorase (of Toyo Jozo) | 5 Units |
| NBT (of Wako Pure Chemical Ind.) | 0.025% |
| KCl | 100 mM |
| Polyoxyethylene (20) sorbitan monooleate (of Wako Pure Chemical Ind.) | 0.5% |
| L-carnitine (of Sigma) | 100 mM |

(b) Determination of enzymatic activity:

1 ml of the reaction solution was placed in a small test tube and incubated at 37° C. for 5 mins. and thereto was added 0.02 ml of the esterase solution to be examined, to cause the reaction, with agitation. After 10 mins. 2 ml of 0.1N aq. HCl were added thereto to terminate the reaction and the $A_{550\ nm}$ of the solution was measured to obtained the absorbance $A_1$.

On the other hand, the same procedures were repeated for a reaction solution in which the L-carnitine was omitted, to obtain the absorbance $A_0$.

(c) Calculation equation:

$$\text{Unit/ml} = \frac{A_1 - A_2}{21.7} \times \frac{1}{10} \times \frac{3.02}{0.02} \times Z$$

(in which Z denotes the dilution magnification ratio and the numeral 21.7 corresponds to the molecular extinction coefficient in $cm^2/\mu mol$).

Example 3

Figure 5:
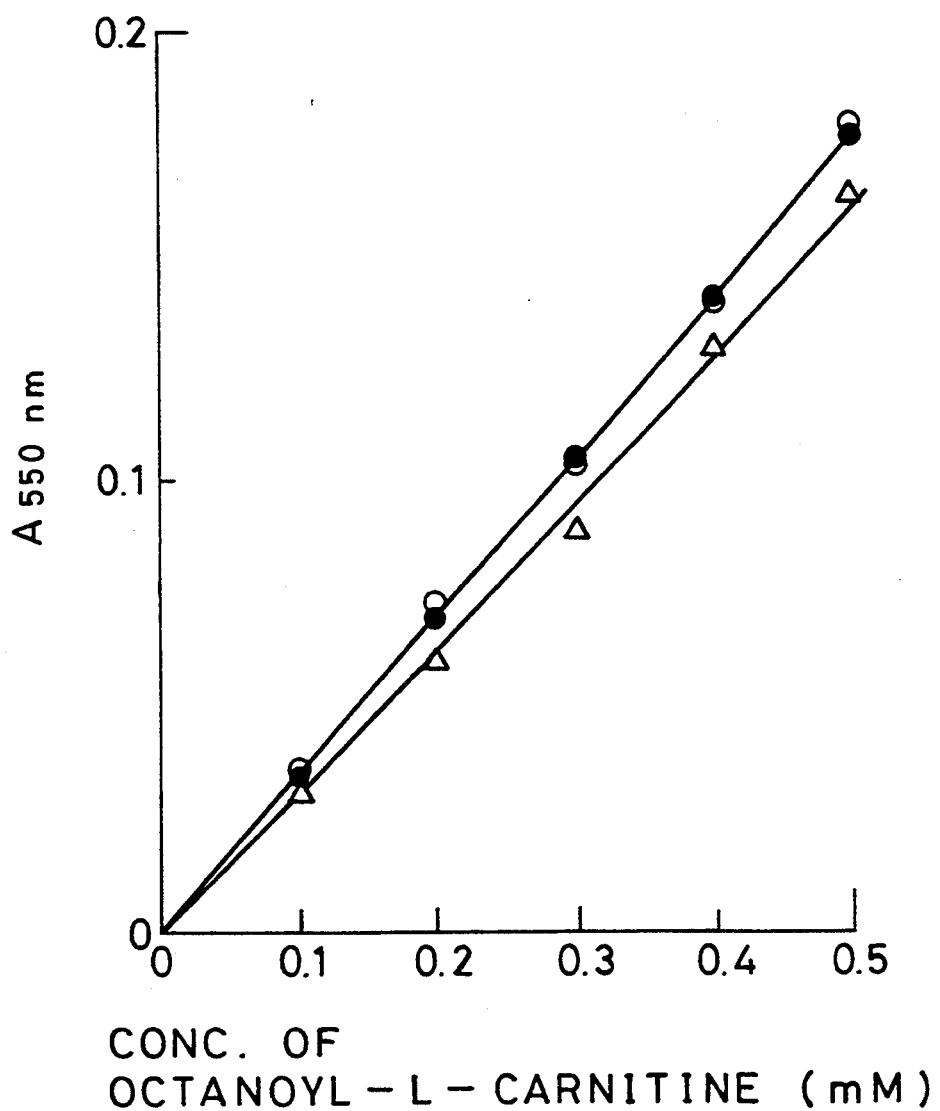
FIG. 5 is a graph comparing the hydrolyzing activity of the acyl-carnitine esterase according to the present invention (indicated with circles) with that of potassium hydroxide (indicated with triangles) for octanoyl-L-carnitine.

Comparison of Hydrolysis Performance of Octanoyl-L-carnitine Produced by the Acyl-carnitine Esterase of the Invention with that of Aq. Potassium Hydroxide Sample solutions of octanoyl-L-carnitine were prepared using 50 mM tris-HCl buffer solution (pH 8.0) in such a way that octanoyl-L-carnitine concentrations of 0.1 mM, 0.2 mM, 0.3 mM, 0.4 mM and 0.5 mM were provided, respectively. 1 ml of each of these solutions was introduced into a small test tube and incubated at 37° C. for 5 mins., after which 0.1 ml of the enzyme solution (0.41 U/ml) prepared in Example 2 was added and the resulting mixture was further incubated for 15 mins. 0.05 ml of each of these enzyme solution-added solutions was then add to 1 ml aliquots of separately prepared reaction solutions of L-carnitine of analytical method A in small test tubes at 37° C. Each of the thus-treated solutions was incubated for 2 mins., and then there was added to each 2 ml of 0.1N aq. HCl and the resulting solution was examined at $A_{550\ nm}$. Parallel thereto, sample solutions were prepared similarly but using KOH solution as the hydrolyzing agent. Thus, 1 ml of 10N KOH solution was added to 1 ml of octanoyl-L-carnitine and the resulting solution was incubated at 37° C. for 3 hours, whereupon the solution was neutralized by adding thereto 1 ml of 10N aq. HCl. 0.15 ml of this neutralized solution was added to 1 ml of the reaction solution of analytical method A, whereupon the resulting solution was examined at $A_{550\ nm}$ in the same manner. The results are shown in the graph of FIG. 5, which shows that octanoyl-L-carnitine had been completely hydrolyzed by the enzyme according to the present invention. In FIG. 5, the marks , Δ and stand for the values obtained by the acyl-carnitine esterase according to the present invention, those obtained by KOH, and those calculated theoretically, respectively.

Example 4

Determination of Acyl-L-carnitine in Human Serum

The amount of free L-carnitine in male human serum was determined by the analysis method A for 5 normal healthy male donors. 1 ml of 10N aq. potassium hydroxide was added to 1 ml of the serum and the mixture was incubated at 37° C. for 2 hours, whereupon this alkali-treated serum was neutralized by adding thereto 1 ml of 10N aq. HCl. The thus-treated serum was examined by analytical method A for its total carnitine content. On the other hand, 1 mg (0.1 U/mg) of acyl-carnitine esterase according to the present invention was added to 1 ml of fresh serum and this esterase-inoculated serum was incubated at 37° C. for 15 mins. This esterase-treated serum was also examined by analytical method A for its total carnitine content. The results are summarized in Table 1. Table 1 shows that acyl-L-carnitines had been hydrolyzed by the esterase according to the present invention about the same as by potassium hydroxide.

TABLE 1

| Serum Sample (Donor Age) | Conc. of Free L-carnitine detected (in μM) | Total L-carnitine Conc. Detected (in μM) Hydrolyzed by | |
|---|---|---|---|
| | | Esterase | KOH |
| 1 (20) | 40.7 | 71.9 | 70.8 |
| 2 (23) | 45.3 | 73.2 | 74.9 |
| 3 (34) | 37.6 | 69.8 | 67.0 |
| 4 (37) | 44.0 | 65.1 | 65.7 |
| 5 (48) | 42.9 | 71.5 | 70.3 |

Reference Example 3

Purification of Acyl-carnitine Esterase Originating from Liver of Rat

For use in a comparison of another esterase performance with that of the esterase according to the present invention, acyl-carnitine esterase was collected from liver of rat and purified according to the technique described by S. Mahadevan and F. Sauer in "J. Biol. Chem.", 244, No 16, 4448–4453 (1969). From the homogenate of 50 g of the rat liver, acyl-carnitine esterase was extracted and purified using DEAE-cellulose (Whatman DE-52) and Sephadex G-200 (supplied by Pharmacia), whereby 101.6 mg (0.364 U/ml) of freeze-dried product was obtained.

Reference Example 4

Using the esterase produced in Reference Example 3, enzymatic activity and Km values for acetyl-carnitine, propionyl-L-carnitine, octanoyl-L-carnitine, decanoyl-L-carnitine and palmitoyl-L-carnitine were determined. The results are given in Table 2. As seen, the esterase does not exhibit enzymatic activity for the short-chain acyl-L-carnitines, i.e. acetyl-L-carnitine and propionyl-L-carnitine, but it does exhibit enzymatic activity for other medium- to long-chain acyl-L-carnitines. The Km values for these acyl-L-carnitines were found to be quite high, i.e. of the order to $10^{-3}$ M, as reported in the literature.

TABLE 2

| Acyl-L-carnitine | Enzymatic Activity (rel. %) | Km Value ($\times 10^{-3}$) |
| --- | --- | --- |
| Acetyl-L-carnitine | 0 | — |
| Propionyl-L-carnitine | 0 | — |
| Octanoyl-L-carnitine | 44 | ca. 3 |
| Decanoyl-L-carnitine | 100 | ca. 2 |
| Palmitoyl-L-carnitine | 27 | ca. 5 |

Example 5

The esterase prepared in Reference Example 3 was examined as to heat stability.

Figure 6:
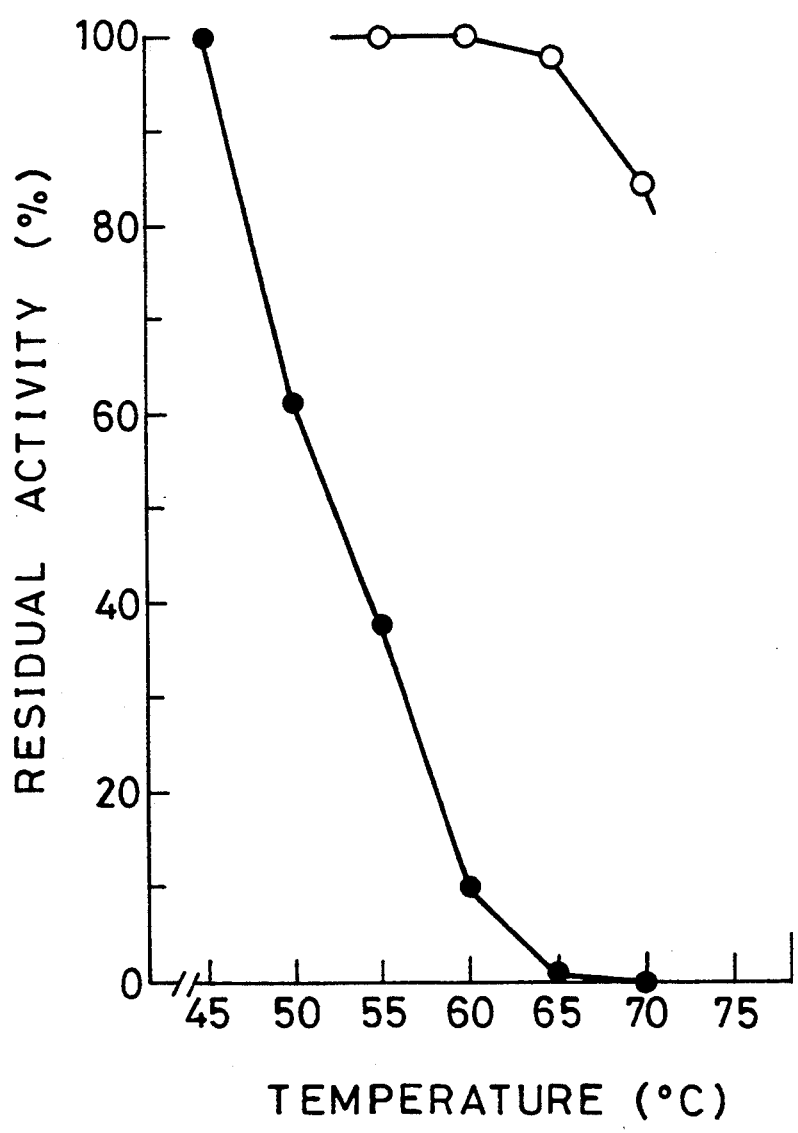
FIG. 6 is a graph comparing the heat stability of the acyl-carnitine esterase according to the present invention (with hollow circles) with that of the acyl-carnitine esterase originating from rat liver (with solid circles)

Aliquot solutions were prepared each comprising 100 mM tris-HCl buffer solution (pH 8.0) and each having an enzyme concentration of 0.1 U/ml. Using these sample solutions, the residual enzymatic activity remaining after a heat treatment at respectively 45° C., 50° C., 55° C., 60° C., 65° C. and 70° C. for 30 mins. was determined. The results are shown on the graph of FIG. 6, from which it is seen that the enzymatic activity decreases to 61% at a temperature of 50° C. In the graph, the plotted marks ● and ○ correspond each to the data for rat-origin esterase and for esterase according to the present invention, respectively.

Example 6

Figure 7:
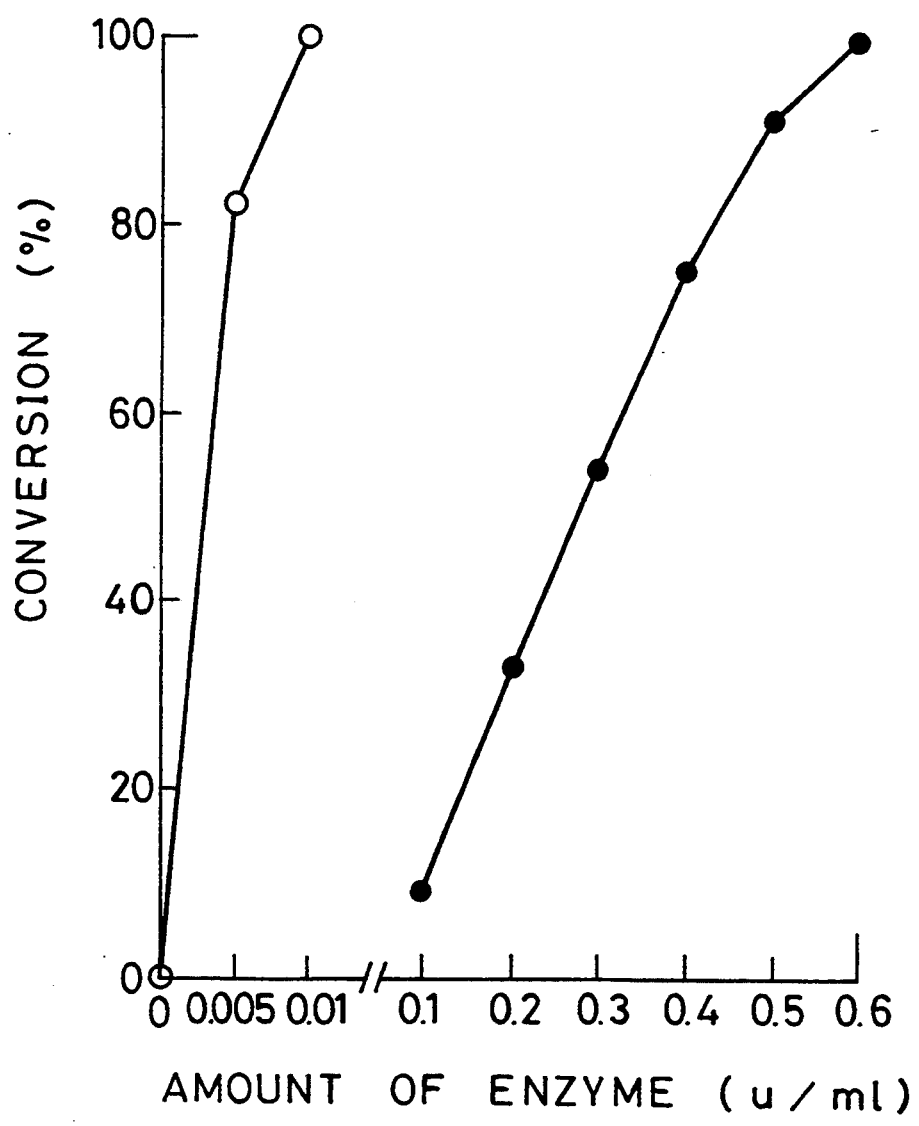
FIG. 7 is a graph comparing the hydrolyzing activity of the acyl-carnitine esterase according to the present invention (indicated with hollow circles) with that of the acyl-carnitine esterase originating from rat liver (indicated with solid circles) for octanoyl-L-carnitine.

1 ml aliquots of the sample solutio prepared from 100 mM tris-HCl solution (pH 8.0) containing 0.02 mM octanoyl-L-carnitine, with varying amounts of esterase originating from liver of rat, prepared in Reference Example 3, and with varying amounts of esterase according to the present invention prepared in Example 2, were subjected to enzymatic hydrolysis at 37° C. for 50 mins. and the amount of thus-formed L-carnitine was determined. The results are shown on the graph of FIG. 7, which shows that the enzymatic hydrolysis had almost been completed at an esterase content of 0.01 U/ml for the esterase according to the present invention, while the enzymatic reaction was not completed for the esterase originating from rat liver even at an esterase content of 0.6 U/ml.

Example 7

Using the purified esterase originating from rat liver and that according to the invention, the analysis of acyl-L-carnitine was carried out. To each 1 ml aliquot of 100 mM tris-HCl buffer solution (pH 8.0) each containing 1 mM of acetyl-L-carnitine, propionyl-L-carnitine, hexanoyl-L-carnitine, octanoyl-L-carnitine, decanoyl-L-carnitine, lauroyl-L-carnitine, myristoyl-L-carnitine, palmitoyl-L-carnitine and stearoyl-L-carnitine, respectively there was added 0.1 U (1 mg) of the esterase according to the present invention and the resulting solutions were incubated at 37° C. for 30 mins. On the other hand, 1 Unit (27.5 mg) of purified esterase originating from rat liver was added to 1 ml of the same acyl-L-carnitine buffer solution and the solution was also incubated at 37° C. for 30 mins. To each of two 1 ml aliquots of the reaction solution of the analytical method A for determining L-carnitine which had been incubated preliminarily at 37° C. for 5 mins., there was added 0.01 ml of one of the reacted esterase solutions prepared as above and the resulting mixtures were incubated at 37° C. for two mins. Thereto was then added 2 ml of 0.1N aq. HCl and absorbance was measured at $A_{550\,nm}$, in order to determine the amount of L-carnitine produced. On the other hand, a reaction solution to which 0.01 ml of the rat-origin esterase solution had been added and incubated, was further treated by adding thereto 0.1 U of the esterase according to the present invention, further incubated at 37° C. for 30 mins., whereupon this supplementally treated solution was examined for absorbance at $A_{550\,nm}$. The results are summarized in Table 3, from which it will be seen that in the sample solutions treated with the esterase according to the present invention, all the acyl-L-carnitine had completely been hydrolyzed, whereas in the sample solutions treated with the esterase originating from rat liver, only the acyl-L-carnitines other than the short-chain acyl-L-carnitines, namely, acetyl-L-carnitine and propionyl-L-carnitine, had been hydrolyzed. By supplemental further treatment with the esterase according to the present invention, the short-chain acyl-L-carnitines are hydrolyzed.

TABLE 3

| Treated by | $A_{550\,nm}$ Observed | Acyl-L-carnitines Determined |
| --- | --- | --- |
| Theoretically | 0.649 | 9.0 mM (100%) |
| Inventive esterase | 0.662 | 9.18 mM (102%) |
| Rat-derived esterase | 0.487 | 6.76 mM (75%) |
| Rat-derived esterase + inventive esterase | 0.636 | 8.82 mM (98%) |

Example 8

To 1 ml of serum of a normal healthy male human donor (Serum Sample 1 in Table 1 of Example 4), 1 U (27.5 mg) of purified esterase originating from rat liver was added and the mixture was incubated at 37° C. for 30 mins., whereby enzymatically hydrolyzed Reacted Liquor 1 was obtained. 0.1 ml of this Reacted Liquor 1 was added to 1 ml of the reaction solution of analytical method A for determining L-carnitine which had been incubated preliminarily at 37° C. for 5 mins., and the resulting solution was incubated at 37° C. for 5 mins., whereupon this incubated solution was observed at $A_{550\,nm}$, whereby $A_{550\,nm}=0.121$ was obtained. On the other hand, a Reacted Liquor 2 was prepared by adding to 0.9 ml of Reacted Liquor 1 0.09 U (0.9 mg) of the esterase according to the present invention and incubating the resulting mixture at 37° C. for 30 mins. This Reacted Liquor 2 was also used for the determination of $A_{550\ nm}$ in the same manner as for Reacted Liquor 1, whereby $A_{550\ nm} = 0.142$ was obtained.

From the above experimental results, the carnitine profile in the serum of male donor 1 is estimated to be as given in the following Table 4.

TABLE 4

| Carnitine | Concentration |
| --- | --- |
| Free L-carnitine | 40.7 μM |
| Total carnitine | 71.9 μM |
| Acyl-L-carnitine | 31.2 μM |
| Medium-long chain acyl-L-carnitines | 20.6 μM |
| Acetyl- and propionyl-L-carnitine | 10.6 μM |

Example 9

Reaction solution composition:
(Ia) 20 mM tris-HCl buffer solution (pH 8.0)
0.2% Polyoxyethylene (20) sorbitan monooleate (Wako Pure Chem. Ind.)
(Ib) 20 mM tris-HCl buffer solution (pH 8.0)
0.2% Polyoxyethylene (20) sorbitan monooleate (Wako Pure Chem. Ind.)
0.2 U/ml Acyl-L-carnitine esterase (from *Alcaligenes sp.* No. 981 supplied by Toyo Jozo)
(Ic) 20 mM tris-HCl buffer solution (pH 8.0)
0.2% Polyoxyethylene (20) sorbitan monooleate (Wako Pure Chem. Ind.)
1 U/ml Acyl-L-carnitine esterase (originating from rat liver)
(III) 200 mM tris-HCl buffer solution (pH 9.5)
8 mg Thio-NAD (supplied by Sigma)
0.2 mM NADH (supplied by Oriental Kobo)
370 U/ml L-carnitine dehydrogenase (from *Alcaligenes sp.* No. 981 supplied by Toyo Jozo)

To 25 ml of the serum of male donor 1, 0.5 ml of the above solution (Ia) and 0.5 ml of the above solution (II) both of which had been incubated preliminarily at 37° C. were added and the mixture was warmed at 37° C. The difference between the data of absorbance at 400 nm determined after 3 mins. and after 5 mins. from the addition of the solution was calculated ($A_{(mAbs)}$). The same procedures were used also for solution (Ib) to calculate the difference of the absorbance data (B). Furthermore, the same procedures ere applied also for distilled water, for the standard 50 μM L-carnitine solution and for the solution (Ia) alone, respectively, without using serum, whereby $R_B$ and S were obtained.

From these results, the free L-carnitine and total carnitine contents are calculated by the following equations:

$$(1)\ \text{Free L-carnitine } (\mu M) = \frac{(B - R_8)}{(S - R_B)} \times 50$$

$$(2)\ \text{Total carnitine } (\mu M) = \frac{(A - R_8)}{(S - R_B)} \times 50$$

Separately therefrom, 25 ml of the above-mentioned serum was added to 0.5 ml of the above solution (Ic) containing acyl-L-carnitine esterase originating from rat liver and the resulting mixture was warmed at 37° C. for 30 mins., in order to cause all the acyl-L-carnitines other than acetyl-L-carnitine and propionyl-L-carnitine to be hydrolyzed. To the thus-treated mixture, 0.5 ml of the above solution (II) was added and the resulting mixture was warmed at 37° C., whereupon the absorbance at 400 nm was observed after 3 mins. and after 5 mins. from the addition of the solution (II), in order to obtain the difference between them by calculation. Total carnitine content except acetyl- and propionyl-L-carnitine is calculated from the following equation:

(3) Total carnitine without acetyl- and
$$\text{propionyl-L-carnitine } (\mu M) = \frac{(B - R_B)}{(S - R_B)} \times 50$$

The content of acetyl-L-carnitine plus propionyl-L-carnitine is calculated from the equation (4) Acetyl- + propionyl-L-carnitine (μM) = (2) − (3)

These results are summarized in the following table. As can be seen, the serum carnitine profile of Sample 1 coincides nearly exactly with the results obtained in Example 8.

| Difference of Absorbances at 400 nm at Times of 3 and 5 minutes from start | | | | |
| --- | --- | --- | --- | --- |
| A | B | C | S | $R_B$ |
| 29 mAbs | 49 mAbs | 41 mAbs | 35 mAbs | 2 mAbs |

| | Acyl-L-carnitine | | |
| --- | --- | --- | --- |
| Total carnitine | Acetyl- and propionyl-L-carnitine | Others | Free L-carnitine |
| 71.2 μM (2) | 30.3 μM 12.1 μM (4) | 18.2 μM | 40.9 μM (1) 59.1 μM (3) |

Example 10

Reaction Mixture:
40 mM tris-HCl buffer solution (pH 8.0)
0.5 % Polyoxyethylene (20) sorbitan monooleate (Wako Pure Chem. Ind.)
5 mM NAD+
50 U L-carnitine dehydrogenase (from *Alcaligenes sp.* No. 981 supplied by Toyo Jozo)
0.1 mM Acetyl-L-carnitine
0.1 mM Octanoyl-L-carnitine Procedure and Results:
1 ml of the above reaction solution was placed in a small test tube and was incubated at 37° C. for 5 mins. Thereto was added 1 U (27.5 mg) of the purified acyl-carnitine esterase originating from rat liver and the resulting solution was again incubated at 37° C. for 30 mins., whereupon this was measured as to $A_{340\ nm}$, which gave the value $A_{340\ nm} = 0.561$. To this solution, 0.025 ml of 5N aq. HCl was added and the resulting acidified solution was incubated at 37° C. for 15 mins., whereupon the solution was neutralized by adding 0.025 ml of 5N aq. KOH and the thus-neutralized solution was measured as to $A_{340\ nm}$, which gave the value of $A_{340\ nm} = 0.08$. To the thus-treated reaction solution, 0.01 ml of 500 mM NAD+, 0.02 ml of L-carnitine dehydrogenase and 0.1 U (1 mg) of the esterase according to the present invention were further added and the resulting mixture was again incubated at 37° C. for 30 mins., whereupon the resulting solution was measured as to $A_{340\ nm}$, which gave the value of $A_{340\ nm} = 0.594$.

As described above, all the acetyl-L-carnitines in the sample solution were determined by first subjecting the sample solution to an enzymatic hydrolysis with the esterase originating from rat liver in order to hydrolyze octanoyl-L-carnitine, then treating the thus-produced L-carnitine with L-carnitine dehydrogenase and NAD+ to convert the L-carnitine into dehydrocarnitine with conversion of NAD into NADH, and thereafter removing the formed NADH by acid decomposition by addition to hydrochloric acid, and finally treating the resulting reaction mixture by renewed addition of the L-carnitine dehydrogenase together with NAD+ and the esterase according to the present invention.

Example 11

Figure 8:
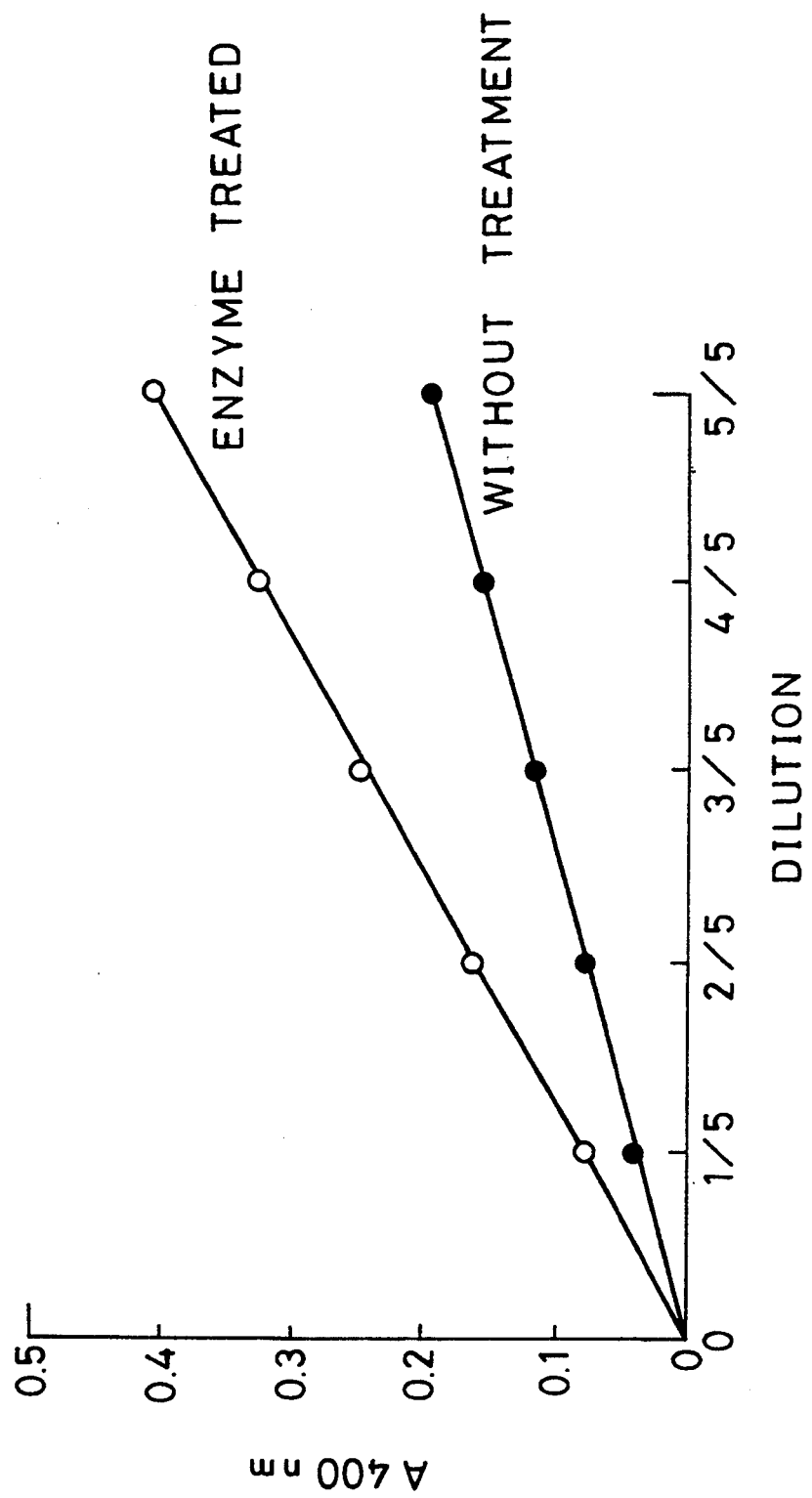
FIG. 8 is a graph showing the applicability of the acyl-carnitine esterase according to the present invention to the quantitative determination of acetyl-L-carnitine.

50 mM glycine-NaOH (pH 10.0)
5 mM thio-NAD (supplied by Sigma)
30 U/ml L-carnitine dehydrogenase (from *Alcaligenes sp.* No. 981 supplied by Toyo Jozo)
0.5 % Polyoxyethylene (20) sorbitan monooleate (Wako Pure Chem. Ind.)
0.1M Sodium chloride A mixed solution consisting of 250 μM of L-carnitine and 250 μM of acetyl-L-carnitine was prepared using 50 mM tris-HCl buffer solution (pH 8.0). This mixed solution was diluted by five different stepwise dilution ratios using the same 50 mM tris-HCl buffer solution (pH 8.0) to obtain five sample solutions having each gradationally different concentration. Each of these five samples was introduced into two test tubes each in an amount of 0.5 ml and the test tubes were warmed preliminarily 37° C. To one test tube was added 0.05 ml of acyl-carnitine esterase solution (0.41 U/ml) of Example 2 (to serve as the enzyme-treated sample) and to the other test tube was added 0.05 ml of distilled water (to serve as the sample without enzyme treatment), whereupon both were warmed at 37° C. for 15 mins. To 1 ml of the reaction solution given above which had preliminarily been warmed at 37° C., there was added respectively 0.1 ml of the above enzyme-treated sample solution (indicated on the graph of FIG. 8 by the mark ○) and the above sample solution without enzyme treatment (indicated on the graph of FIG. 8 by the mark ●), whereupon the resulting solution was warmed at 37° C. for 10 mins. and the thus-treated solution was measured for absorbance at 400 nm.

For the blank test, 15 mM tris-HCl buffer solution (pH 8.0) was employed in place of the sample solution. On the graph in FIG. 8, the values resulting when the blank test values have been subtracted from the observed values, are plotted.

What is claimed is:

1. A method of assaying for acyl-L-carnitines comprising short-chain acyl-carnitines in a biological or alimentary specimen whose acyl-L-carnitine content is to be determined, comprising subjecting a sample of said specimen to enzymatic hydrolysis with a first acyl-carnitine esterase which catalyzes the hydrolysis reaction of one mole of each of the acyl-L-carnitines with one mole of water to form one mole of the corresponding fatty acid and one mole of L-carnitine, and then determining the amount of the fatty acid and L-carnitine thus formed;

said first acyl-L-carnitine esterase having the following properties:
molecular weight of 63000±7000,
isoelectric point of pH 5.1±0.5,
optimum pH of about pH 8,
pH stability at least within a range of pH 7.5 to 8.5,
optimum temperature of about 70° C.
and substrate specificity for short-chain acyl-carnitines comprising acetyl-L-carnitine and propionyl-L-carnitine and medium-to-long-chain acyl-carnitines comprising hexanoyl-, octanoyl-, decanoyl-, lauroyl-, myristoyl-, palmitoyl-, and stearoyl-carnitine said first acyl-L-carnitine esterase being that produced by *Alcaligenes sp.* FERM BP-2570.

2. A method of assaying for acyl-L-carnitine as claimed in claim 1, wherein a determination of the amount of the resulting fatty acid is carried out by liquid chromatography or gas chromatography.

3. A method of assaying for acyl-L-carnitines as claimed in claim 1, wherein the determination of the amount of L-carnitine is carried out by subjecting said L-carnitine to the action of a reagent composed of an L-carnitine dehydrogenase and a nicotinamide adenine dinucleotide group (NAD group) or a thionicotinamide adenine dinucleotide group (thio-NAD group), and then determining the amount of the resulting reduced NAD group or thio-NAD group.

4. A method of assaying for acyl-L-carnitines as claimed in claim 1, wherein said reagent contains an L-carnitine dehydrogenase and a combination of either (1) a NAD group with a reduced thio-NAD group or (2) a thio-NAD group with a reduced NAD group, for effecting a cycling reaction expressed by the reaction scheme

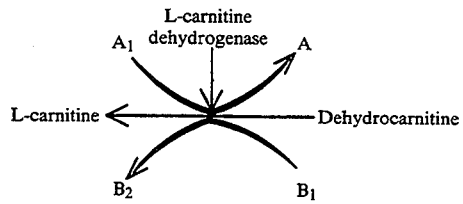

in which $A_1$ denotes said NAD group or thio-NAD group, $A_2$ denotes the corresponding reduced product of $A_1$, $B_1$ represents a reduced thio-NAD group when $A_1$ denotes a NAD group or represents a reduced NAD group when $A_1$ denotes a thio-NAD group and $B_2$ represents the corresponding oxidized product of $B_1$, and then determining the amount of $B_1$ consumed during the cycling reaction and the amount of $A_2$ formed during the cycling reaction.

5. A method of assaying for short-chain acyl-L-carnitine in a biological or alimentary specimen whose acyl-L-carnitine content is to be determined, comprising the steps of (a) subjecting a first sample of said specimen to enzymatic hydrolysis with a first acyl-carnitine esterase which has no enzymatic activity for acetyl-L-carnitine and propionyl-L-carnitine but which has substrate-specificity for acyl-L-carnitines of medium chain lengths to long chain lengths and catalyzes the hydrolysis of one mole of each acyl-L-carnitine of said medium chain lengths to long chain lengths with one mole of water to form one mole of the corresponding fatty acid and one mole of L-carnitine, and then determining the amount of the fatty acid and/or L-carnitine thus formed;

(b) subjecting a second sample of said specimen to enzymatic hydrolysis with a second acyl-carnitine esterase which catalyzes the hydrolysis of one mole of each of the acyl-L-carnitines with one mole of water to form one mole of the corresponding fatty acid and one mole of L-carnitine, and then determining the amount of the fatty acid or L-carnitine thus formed; said second acyl-L-carnitine esterase having the following properties:
molecular weight of 63000±7000,
isoelectric point of pH 5.1±0.5,
optimum pH of about pH 8,
pH stability at least within a range of pH 7.5 to 8.5,
optimum temperature of about 70° C.
and substrate specificity for short-chain acyl-carnitines comprising acetyl-L-carnitine and propionyl-L-carnitine and medium-to-long-chain acyl-carnitines comprising hexanoyl-, octanoyl-, decanoyl-, lauroyl-, myristoyl-, palmitoyl-, and stearoyl-carnitine
said second acyl-L-carnitine esterase being that produced by *Alcaligenes sp.* FERM BP-2750; and
(c) evaluating the difference in the amounts of fatty acid or L-carnitine determined in the above process steps (a) and (b) thereby to determine an amount of said short-chain acyl-carnitines in said specimen.

6. A method of assaying for short chain acyl-L-carnitines as claimed in claim 5, wherein said first acyl-carnitine esterase is an acyl-carnitine esterase of rat origin.

7. A method of assaying for short acyl-L-carnitine as claimed in claim 5, wherein a determination of the amount of the resulting fatty acid is carried out by liquid chromatography or gas chromatography.

8. A method of assaying for short chain acyl-L-carnitines as claimed in claim 5, wherein the determination of the amount of L-carnitine is carried out by subjecting the enzymatic hydrolysis product to the action of a reagent composed of an L-carnitine dehydrogenase and an NAD group or thio-NAD group, and then determining the amount of the resulting reduced NAD group or reduced thio-NAD group.

9. A method of assaying for short-chain acyl-L-carnitines as claimed in claim 8, wherein said reagent contains an L-carnitine dehydrogenase and a combination of either (1) an NAD group with a reduced thio-NAD group or (2) a thio-NAD group with a reduced NAD group, for effecting a cycling reaction expressed by the reaction scheme

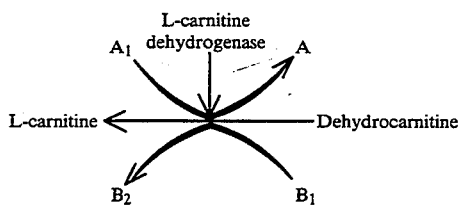

in which $A_1$ denotes said NAD group or thio-NAD group, $A_2$ denotes the corresponding reduced form of $A_1$, $B_1$ represents the reduced thio-NAD group when $A_1$ denotes an NAD group or represents the reduced NAD group when $A_1$ denotes a thio-NAD group, and $B_2$ represents the corresponding oxidized product of $B_1$, and then determining the amount of $B_1$ consumed during the cycling reaction and the amount of $A_2$ formed during the cycling reaction.

10. A method of assaying for short chain acyl-L-carnitines as claimed in claim 8, wherein said reagent contains an L-carnitine dehydrogenase and a combination of either (1) a NAD group with a reduced thio-NAD group or (2) a thio-NAD group with a reduced NAD group, to perform a cycling reaction expressed by the reaction scheme

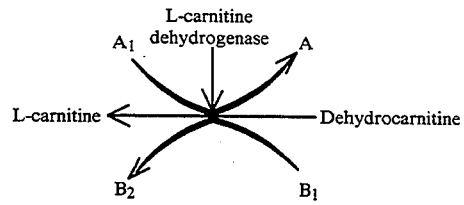

in which $A_1$ denotes said NAD group or thio-NAD group, $A_2$ denotes the corresponding reduced product of $A_1$, $B_1$ represents a reduced thio-NAD group when $A_1$ denotes a NAD group or represents a reduced NAD group when A denotes a thio-NAD group and $B_2$ represents the corresponding oxidized product of $B_1$, and then determining the amount of $B_1$ consumed during the cycling reaction and the amount of $A_2$ formed during the cycling reaction.

11. A method of assaying for short-chain acyl-L-carnitines in a biological or alimentary specimen whose acyl-L-carnitine content is to be determined, comprising the steps of
(a₁) subjecting a sample of said specimen to the action of a first acyl-carnitine esterase which has no enzymatic activity for acetyl-L-carnitine and propionyl-L-carnitine but which has substrate-specificity for acyl-L-carnitines of medium chain lengths to long chain lengths and catalyzes the hydrolysis of one mole of each of said acyl-L-carnitine of medium chain length to long chain length with one mole of water to form one mole of the corresponding fatty acid and one mole of L-carnitine, then subjecting the resulting reacted sample mixture to the action of a combination of an L-carnitine dehydrogenase with a coenzyme $A_1$ wherein $A_1$ denotes NAD or thio-NAD to convert $A_1$ into a reduced product $A_2$, and treating the resulting sample mixture so as to cause decomposition of the resulting $A_2$,
(b₁) subjecting the resulting reacted sample mixture to the action of a second acyl-carnitine esterase which catalyzes the hydrolysis of one mole of each of the short-chain acyl-L-carnitines with one mole of water to form one mole of the corresponding fatty acid and one mold of L-carnitine,
said second acyl-L-carnitine esterase having the following properties:
molecular weight of 63000±7000,
isoelectric point of pH 5.1±0.5,
optimum pH of about pH 8,
pH stability at least within a range of pH 7.5 to 8.5,
optimum temperature of about 70° C.
and substrate specificity for short-chain acyl-carnitines comprising acetyl-L-carnitine and propionyl-L-carnitine and medium-to-long-chain acyl-carnitines comprising hexanoyl-, octanoyl-, decanoyl-, lauroyl-, myristoyl-, palmitoyl-, and stearoyl-carnitine
said second acyl-L-carnitine esterase being that produced by *Alcaligenes sp.* FERM BP-2570; and determining the amount of the fatty acid or L-carnitine thus formed.

12. A method of assaying for short chain acyl-L-carnitines as claimed in claim 11, wherein a determination of the resulting fatty acid is carried out by liquid chromatography or gas chromatography.

13. A method of assaying for short chain acyl-L-carnitines as claimed in claim 11, wherein the determination of the amount of L-carnitine is carried out by subjecting the enzymatic hydrolysis reaction product to the action of a reagent composed of an L-carnitine dehydrogenase and a NAD group or thio-NAD group, and then determining the amount of the resulting reduced NAD group or reduced thio-NAD group.

* * * * *